US009278121B2

(12) United States Patent
Song et al.

(10) Patent No.: US 9,278,121 B2
(45) Date of Patent: Mar. 8, 2016

(54) METHODS OF USE FOR AN ANTIMICROBIAL PEPTIDE

(71) Applicant: Board of Trustees University of Arkansas, Little Rock, AR (US)

(72) Inventors: Peter I. Song, Little Rock, AR (US); Cheryl Armstrong, Little Rock, AR (US); Sunhyo Ryu, Little Rock, AR (US); Yoonkyung Park, Gwangju (KR); Kyung-soo Hahm, Gwangju (KR)

(73) Assignees: The Board of Trustees of the University of Arkansas, Little Rock, AK (US); Chosun University (KR)

( * ) Notice: Subject to any disclaimer, the term of this patent is extended or adjusted under 35 U.S.C. 154(b) by 0 days.

(21) Appl. No.: 13/803,678

(22) Filed: Mar. 14, 2013

(65) Prior Publication Data

US 2014/0274879 A1 Sep. 18, 2014

(51) Int. Cl.
*A61K 38/16* (2006.01)

(52) U.S. Cl.
CPC .................................... *A61K 38/164* (2013.01)

(58) Field of Classification Search
CPC ................................................... A61K 38/164
See application file for complete search history.

(56) References Cited

U.S. PATENT DOCUMENTS

| 8,410,046 | B2 * | 4/2013 | Hahm et al. | 514/2.4 |
| 2011/0053834 | A1 * | 3/2011 | Hahm et al. | 514/2.4 |
| 2012/0277199 | A1 | 11/2012 | Ye et al. | |

FOREIGN PATENT DOCUMENTS

| WO | WO 2010/061984 | * | 6/2010 | ........... C07K 14/205 |
| WO | 2014152437 A2 | | 9/2014 | |

OTHER PUBLICATIONS

Lee et al., 2012, Antimicrobial HPA3NT3 peptide analogs: Placement of aromatic rings and positive charges are key determinants for cell selectivity and mechanism of action, Biochimica et Biophysica Acta, 1828: 443-454.*
Gopal et al., 2012, Applications of Circular Dichroism for Structural Analysis of Gelatin and Antimicrobial Peptides, Int J Mol Sci, 13: 3229-3244.*
Park et al., 2011, Selective Algicidal Action of Peptides against Harmful Algal Bloom Species, PLoS ONE, 6(10): 10 pages.*
Gopal et al., 2009, Effect of Leucine and lysine substitution on the antimicrobial activity and evaluation of the mechanism of the HPA3NT3 analog peptide, Journal of Peptide Science, 15: 589-594.*
Park et al., 2008, Amphipathic _-helical peptide, HP (2-20), and its analogues derived from Helicobacter pylori: Pore formation mechanism in various lipid compositions, 1778: 229-241.*
Akaza et al., 2009, Effects of Propionibacterium acnes on various mRNA expression levels in normal human epidermal keratinocytes in vitro, Journal of Dermatology, 36: 213-223.*
Pasparakis, "Role of NF-kB in epithelial biology", Immunological Reviews, 2012, pp. 346-358, vol. 246.
Pickert et al., "An evaluation of dapsone gel 5% in the treatment of acne vulgaris", Expert Opin. Pharmacother., 2009, pp. 1515-1521, vol. 10, No. 9.
Putsep, "Antibacterial peptide from *H. pylori*", Nature, 1999, pp. 671-672, vol. 398.
Rock et al., "A family of human receptors structurally related to Drosophila Toll", Proc. Natl. Acad. Sci. USA, 1998, pp. 588-593, vol. 95.
Rossolini et al., "Treatment and control of severe infections caused by multiresistant *Pseudomonas aeruginosa*", Clinical Microbiology and Infection, 2005, pp. 17-32, vol. 11, Supplement 4.
Song et al., "Human Keratinocytes Express Functional CD14 and Toll-Like Receptor 4", The Journal of Investigative Dermatology, 2002, pp. 424-432, vol. 119, No. 2.
Steiner et al., "Pillars Article: Sequence and Specificity of Two Antibacterial Proteins Involved in Insect Immunity", Nature, 1981, pp. 246-248, vol. 292.
Torchia et al., "Segmental Acne versus Mosaic Conditions with Acne Lesions", Dermatology, 2012, pp. 10-14, vol. 224.
Torczynski et al., "Cloning and Sequencing of a Human 18S Ribosomal RNA Gene", DNA, 1985, pp. 283-291, vol. 4, No. 4.
Tosteson et al., "Solid-Phase Synthesis of Melittin: Purification and Functional Characterization", Biochemistry, 1987, pp. 6627-6631, vol. 26, No. 21.
Tuomanen et al., "Microbiological and Clinical Significance of a New Property of Defective Lysis in Clinical Strains of Pneumococci", The Journal of Infectious Diseases, 1988, pp. 36-43, vol. 158, No. 1.
Tzellos et al., "Treating acne with antibiotic-resistant bacterial colonization", Expert Opinion on Pharmacotherapy, 2011, pp. 1233-1247, vol. 12, No. 8.
Wade et al., "Antibacterial peptides designed as analogs or hybrids of cecropins and melittin", Int. J. Pept. Prot. Res., 1992, pp. 429-436, vol. 40.
Zasloff, "Antimicrobial peptides of multicellular organisms", Nature, 2002, pp. 389-395, vol. 415.
Andrews, "Determination of minimum inhibitory concentrations", Journal of Antimicrobial Chemotherapy, 2001, pp. 5-16, vol. 48, Suppl. S1.
Baggiolini et al., "Interleukin-8, a chemotactic and inflammatory cytokine", Federation of European Biochemical Societies, 1992, pp. 97-101, vol. 307, No. 1.
Bevins et al., "Peptides from Frog Skin", Annu. Rev. Biochem., 1990, pp. 395-414, vol. 59.

(Continued)

*Primary Examiner* — Amber D Steele
(74) *Attorney, Agent, or Firm* — Polsinelli PC

(57) ABSTRACT

The present invention encompasses methods for treating an infection and/or treating or reducing inflammation through the administration of a therapeutically effective amount of a peptide to a subject in need thereof. In some aspects, the peptide is a *Helicobacter pylori*-derived peptide, such as an HPA3NT3 peptide and the infection is a bacterial infection.

8 Claims, 12 Drawing Sheets
(7 of 12 Drawing Sheet(s) Filed in Color)

(56) References Cited

OTHER PUBLICATIONS

Blaser, "*Helicobacter pylori*: microbiology of a 'slow' bacterial infection", Trends in Microbiology, 1993, pp. 255-260, vol. 1, No. 7.

Boman et al., "Cell-Free Immunity in Insects", Ann. Rev. Microbiol., 1987, pp. 103-126, vol. 41.

Boman et al., "Antibacterial and antimalarial properties of peptides that are cecropin-melittin hybrids", Federation of European Biochemical Societies, 1989, pp. 103-106, vol. 259, No. 1.

Boman, "Antibacterial Peptides: Key Components Needed in Immunity", Cell, 1991, pp. 205-207, vol. 65.

Boman, "Peptide Antibiotics and Their Role in Innate Immunity", Ann. Rev. Immunol., 1995, pp. 61-92, vol. 13.

Bylund et al., "Proinflannmatory Activity of a Cecropin-Like Antibacterial Peptide from *Helicobacter pylori*", Antimicrobial Agents and Chemotherapy, 2001, pp. 1700-1704, vol. 45, No. 6.

Charakida et al., "Safety and side effects of the acne drug, oral isotretinoin", Expert Opin. Drug. Saf., 2004, pp. 119-129, vol. 3, No. 2.

Cintas et al., "Enterocins L50A and L50B, Two Novel Bacteriocins from *Enterococcus faecium* L50, Are Related to Staphylococcal Hemolysins", Journal of Bacteriology, 1998, pp. 1988-1994, vol. 180, No. 8.

Del Rosso et al., "Optimizing Use of Oral Antibiotics in Acne Vulgaris", Dermatol. Clin., 2009, pp. 33-42, vol. 27.

Dhawan, "Comparison of 2 Clindamycin 1%-Benzoyl Peroxide 5% Topical Gels Used Once Daily in the Management of Acne Vulgaris", Cutis, 2009, pp. 265-272, vol. 83.

Dispenza et al., "Systemic isotretinoin therapy normalizes exaggerated TLR-2-mediated innate immune responses in acne patients", J. Invest. Dermatol., 2012, pp. 2198-2205, vol. 132, No. 9.

Gaitanis et al., "The range of molecular methods for typing Malassezia", Current Opinion in Infectious Diseases, 2009, pp. 119-125, vol. 22.

Gopal et al., "Effect of Leucine and Lysine substitution on the antimicrobial activity and evaluation of the mechanism of the HPA3NT3 analog peptide", Journal of Peptide Science, 2009, pp. 589-594, vol. 15.

Grange et al., "Nicotinamide inhibits Propionibacterium acnes-induced IL-8 production in keratinocytes through the NF-kB and MAPK pathways", Journal of Dermatological Science, 2009, pp. 106-112, vol. 56.

Habermann, "Bee and Wasp Venoms", Science, 1972, pp. 314-322, vol. 177, No. 4046.

Handwerger et al., "Antibiotic Tolerance Among Clinical Isolates of Bacteria", Reviews of Infectious Diseases, 1985, pp. 368-386, vol. 7, No. 3.

International Search Report and Written Opinion from related International Application No. PCT/US14/27340, dated Oct. 3, 2014; 11 pgs.

Katsuta et al., "Unsaturated Fatty Acids Induce Calcium Influx into Keratinocytes and Cause Abnormal Differentiation of Epidermis", The Journal of Investigative Dermatology, 2005, pp. 1008-1013, vol. 124.

Kim, "Review of the Innate Immune Response in Acne vulgaris: Activation of Toll-Like Receptor 2 in Acne Triggers Inflammatory Cytokine Responses", Dermatology, 2005, pp. 193-198, vol. 211.

Kim et al., "Antibacterial and anti-inflammatory effects of Jeju medicinal plants against acne-inducing bacteria", J. Gen. Appl. Microbiol., 2008, pp. 101-106, vol. 54.

Lai et al., "AMPed Up immunity: how antimicrobial peptides have multiple roles in immune defense", Trends Immunol., 2009, pp. 131-141, vol. 30, No. 3.

Lee et al., "Design of novel analogue peptides with potent antibiotic activity based on the antimicrobial peptide, HP (2-20), derived from N-terminus of *Heliocobacter pylori* ribosomal protein L1", Biochimica et Biophsica Acta, 2002, pp. 185-194, vol. 1598.

Lee et al., "Antifungal Mechanism of an Antimicrobial Peptide, HP (2-20), Derived from N-Terminus of *Helicobacter pylori* Ribosomal Protein L1 against *Candida albicans*", Biochemical and Biophysical Research Communications, 2002, pp. 1006-1013, vol. 291, No. 4.

Lee et al., "Sebocytes Express Functional Cathelicidin Antimicrobial Peptides and Can Act to Kill Propionibacterium Acnes", Journal of Investigative Dermatology, 2008, pp. 1863-1866, vol. 128.

Liss et al., "Economic Evaluations of Antibiotic Use and Resistance—A Perspective: Report of Task Force 6", Reviews of Infectious Diseases, 1987, pp. S297-S312, vol. 9, Supplement 3.

Liu et al., "Penicillin Tolerance in Multiply Drug-Resistant Natural Isolates of *Streptococcus pneumoniae*", The Journal of Infectious Diseases, 1985, pp. 365-372, vol. 152, No. 2.

McInturff et al., "Granulysin-Derived Peptides Demonstrate Antimicrobial and Anti-Inflammatory Effects Against Propionibacterium acnes", The Journal of Investigative Dermatology, 2005, pp. 256-263, vol. 125, No. 2.

Merrifield, "Solid Phase Peptide Synthesis. I. The Synthesis of a Tetrapeptide", J. Am. Chem. Soc., 1963, pp. 2149-2154, vol. 85.

Miyasaki et al., "β-sheet antibiotic peptides as potential dental therapeutics", International Journal of Antimicrobial Agents, 1998, pp. 269-280, vol. 9.

Nagy et al., "Distinct Strains of Propionibacterium acnes Induce Selective Human β-Defensin-2 and Interleukin-8 Expression in Human Keratinocytes Through Toll-Like Receptors", The Journal of Investigative Dermatology, 2005, pp. 931-938, vol. 124, No. 5.

"National Nosocomial Infections Surveillance (NNIS) System Report, data summary from Jan. 1992 through Jun. 2004, issued Oct. 2004", Am. J. Infect. Control, 2004, pp. 470-485, vol. 32, No. 8.

Ohsaki et al., "Antitumor Activity of Magainin Analogues against Human Lung Cancer Cell Lines", Cancer Research, 1992, pp. 3534-3538, vol. 52.

Oo et al., "Evaluation of synergistic activity of bovine lactoferricin with antibiotics in corneal infection", Journal of Antimicrobial Chemotherapy, 2010, pp. 1243-1251, vol. 65, No. 6.

Park et al., "Antibiotic activity of Leu-Lys rich model peptides", Biotechnology Letters, 2003, pp. 1305-1310, vol. 25.

Park et al., "A Leu-Lys-rich antimicrobial peptide: activity and mechanism", Biochimica et Biophysica Acta, 2003, pp. 172-182, vol. 1645.

Park et al., "Synergism of Leu-Lys rich antimicrobial peptides and chloramphenicol against bacterial cells", Biochimica et Biophysica Acta, 2006, pp. 24-32, vol. 1764.

Park et al., "Influence of the N- and C-terminal Regions of Leu-Lys Rich Antimicrobial Peptide on Antimicrobial Activity", Protein Pept Letters, 2008, pp. 188-192, vol. 15.

\* cited by examiner

METHODS OF USE FOR AN ANTIMICROBIAL PEPTIDE

GOVERNMENT SUPPORT

This invention was made with government support under RO1 AR052643 awarded by the NIH. The government has certain rights in the invention.

FIELD

The invention relates to methods of treating one or more conditions in animals via administration of an antimicrobial peptide. In particular, the invention relates to the treatment of infections and/or inflammation via administration of an antimicrobial peptide derived from *Helicobacter pylori*.

BACKGROUND

Antimicrobial peptides have recently emerged as potentially potent treatments for several medical conditions. In particular, it has been know that endogenous antimicrobial peptides (i.e., endogenously produced by a particular organism, such as human), such as defensins and cathelicidins may be induced by infection, inflammation, and other injury to function in both adaptive and innate immune responses. For example, these endogenous antimicrobial peptides possess bactericidal properties with respect to both Gram-positive and Gram-negative bacteria. However, given the continued prevalence of infectious diseases and other medical conditions, these endogenous antimicrobial peptides are not completely sufficient for meeting treatment and preventative needs associated with challenges facing modern medicine.

The continued proliferation of antibiotic-resistant infectious agents (e.g., bacterial, fungi, protozoa, viruses, etc.) has driven research in new directions, including the development of exogenous antimicrobial peptides. These antimicrobial peptides may be derived from a variety of organisms, including bacteria, insects, viruses, animals, and plants. Current research efforts have focused on using some of these exogenous antimicrobial peptides in the development of treatment regimens or preventative measures to address some of the ongoing needs in the medical field. The present invention provides methods of using certain antimicrobial peptides in treating infections and reducing and/or treating inflammation.

SUMMARY

One aspect of the invention includes a method of effectively treating an infection, which comprises administering a therapeutically effective amount of an HPA3NT3 peptide to an animal with the infection. In some aspects, the infection may be caused by bacteria, viruses, fungi, including yeast, protozoa, or any combination thereof. For example, the infection could be caused by Gram-positive bacteria or Gram-negative bacteria. By way of example only, the bacterial infection may be caused by organisms such as *Propionibacterium acnes*, *Staphylococcus aureus*, or *Pseudomonas aeruginosa*. However, as mentioned above, the infection could be caused by other unicellular or multi-cellular organisms. Moreover, at least some of the organisms for which the HPA3NT3 peptide is used as a treatment are resistant to one or more conventional antibiotics.

In some aspects, the HPA3NT3 peptide exerts a deleterious effect on the organism causing the infection. For example, the HPA3NT3 peptide exhibits bacteriostatic and/or bactericidal properties such that this peptide may be used to treat bacterial infections. In other aspects, the HPA3NT3 peptide also exhibits antifungal properties such that it may also be used to treat fungal infections.

Some aspects of the invention encompass a method of reducing or treating inflammation in an animal by administering a therapeutically effective amount of the HPA3NT3 peptide to the animal. In some particular aspects, the HPA3NT3 peptide may exhibit an anti-inflammatory effect on at least some of the cells of the animal. For example, after administration, the HPA3NT3 peptide functions to reduce the production of inflammatory mediators such as cytokines, chemokines, and the like. Moreover, the HPA3NT3 peptide also functions to augment intracellular signaling pathways to provide the anti-inflammatory effect. In some aspects, administration of the HPA3NT3 peptide may lead to a reduction in the expression of cell membrane-based receptors, such as pattern-recognition receptors. In response to some of these effects associated with the HPA3NT3 peptide, the animal or portions of the animal may experience reductions in inflammation-based symptoms, such as a reduction of erythema, swelling, cell infiltrate, and the like.

In some aspects, the animal receiving the therapeutically effective amounts of the HPA3NT3 peptide to treat or prevent inflammation need not be currently infected with one of the above-mentioned organisms. Although an infection is a well-known inducer of inflammation, in some aspects, the animal may be presenting inflammation stemming from an injury, improper regulation of the immune system, or any other non-infection-based source of inflammation. Accordingly, regardless of the origin of the inflammation, a therapeutically effective amount of the HPA3NT3 peptide may be used to reduce or treat inflammation in the animal.

In some aspects, the therapeutically effective amount of the HPA3NT3 peptide may be administered in different manners. In particular, the HPA3NT3 peptide may be administered in the form of a topical composition. For example, the topical composition may take the form of one or more of a liquid solution, a semi-solid solution, a cream, an ointment, a gel, or any other known formulation that may be topically applied. In some aspects, the topical composition is applied to the skin of the animal. In other aspects, the topical composition is applied to other portions of the animal, such as the eyes or ears (e.g., intratympanically). In yet other aspects, the HPA3NT3 peptide is formulated for administration via an injection (e.g., intradermal injection).

Some aspects of the invention encompass a method of treating an infection and infection-induced inflammation in non-immortalized cells, which comprises administering a therapeutically effective amount of an HPA3NT3 peptide to the non-immortalized cells. In particular, non-immortalized cells may include any cell types that do not proliferate indefinitely either through human intervention or a disease state, such as cancer. For example, non-immortalized cells may include primary cells such as keratinocytes, dermal microvascular endothelial cells, corneal epithelial cells, and dermal fibroblasts.

Additional objectives, advantages and novel features will be set forth in the description which follows or will become apparent to those skilled in the art upon examination of the drawings and detailed description which follows.

BRIEF DESCRIPTION OF THE DRAWINGS

The application file contains at least one drawing executed in color. Copies of this patent application publication with color drawings will be provided by the Office upon request and payment of the necessary fee.

Figure 1:
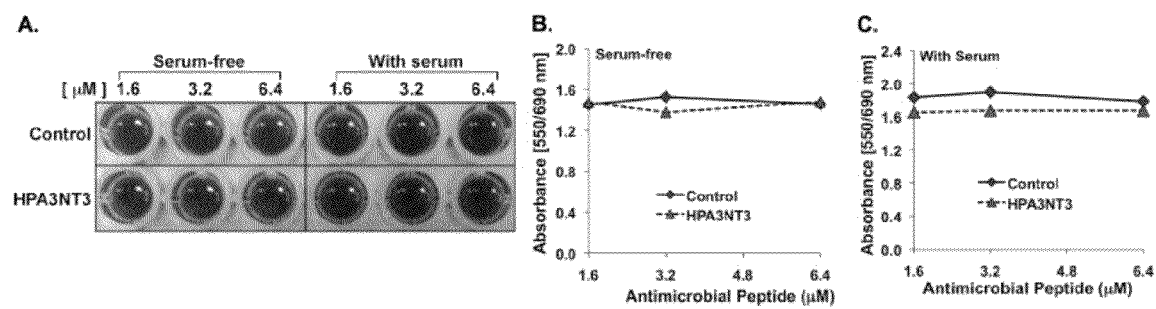
FIG. 1A depicts the effect of the HPA3NT3 peptide on human keratinocytes cells (HK cell) viability as measured using an MTT assay. This figure depicts wells from a 96-well microtiter plate that contain HK cells that have been incubated with a solution of 1.6, 3.2, or 6.4 µM HPA3NT3 peptide or a negative control and then stained with MTT with or without the presence of serum.
FIGS. 1B and 1C graphically depict HK cell viability after incubation with a solution of 1.6, 3.2, or 6.4 µM HPA3NT3 peptide or a negative control as measured by a spectrophotometric absorbance ratio of 550 nm/690 nm.

The headings used in the figures should not be interpreted to limit the scope of the claims.

DETAILED DESCRIPTION

Applicants have discovered methods of using an antimicrobial peptide as an effective treatment for infections and related symptoms and/or the treatment of inflammation and related symptoms. The methods may include administering a therapeutically effective amount of the antimicrobial peptide to a subject in need thereof. The present invention encompasses the discovery that some antimicrobial peptides provide an effective treatment for certain medical conditions, including infections and inflammation. Moreover, in some aspects, the inflammation may arise as a symptom of the infection or it may arise as a result of non-infection-based origins (e.g., physical injury).

In an aspect, the antimicrobial peptide is derived from an organism. In some aspects, the organism is a prokaryote. Moreover, in some aspects the organism is *Helicobacter pylori*. For example, the antimicrobial peptide may be derived from HP(2-20), an endogenous antimicrobial peptide produced by *H. pylori*, which is in turn derived from amino acids 2-20 of ribosomal protein L1 of *H. pylori*. Bylund, J. et al., Proinflammatory Activity of a Cecropin-like Antibacterial Peptide from Helicobacter Pylori, 45 ANTIMICROB AGENTS CHEMOTHER 1700-1704 (2001). In some aspects, the antimicrobial peptide is HPA3NT3, which includes the amino acid sequence of SEQ. ID NO: 1. Gopal, R. et al., Effect of Leucine and Lysine Substitution on the Antimicrobial Activity and Evaluation of the Mechanism of the HPA3NT3 Analog Peptide, 15 JOURNAL OF PEPTIDE SCIENCE: AN OFFICIAL PUBLICATION OF THE EUROPEAN PEPTIDE SOCIETY 589-594 (2009); Park, Y. et al., A Leu-Lys Rich Antimicrobial Peptide: Activity and Mechanism, 1645 BIOCHIM BIOPHYS ACTA 172-182 (2003); Park, Y. et al., Antibiotic Activity of Leu-Lys Rich Model Peptides, 25 BIOTECHNOL LETT 1305-1310 (2003); Park, Y. et al., Synergism of Leu-LysRich Antimicrobial Peptides and Chloramphenicol Against Bacterial Cells, 1764 BIOCHIM BIOPHYS ACTA 24-32 (2006); Park, H. K. et al., Influence of the N- and C-terminal Regions of Leu-Lys Rich Antimicrobial Peptide on Antimicrobial Activity, 15 PROTEIN PEPT LETT 188-192 (2008); and Zasloff, M., Antimicrobial Peptides of Multicellular Organisms, 415 NATURE 389-395 (2002).

As used herein, the terms "treating" or "treatment" include prevention, attenuation, reversal, or improvement in at least one symptom or indicator of infection-associated and/or inflammation-associated symptoms.

As used herein, the term "therapeutically effective amount" refers to an amount effective, at dosages and for periods of time necessary, to achieve the desired therapeutic result. A therapeutically effective amount of HPA3NT3 peptide may be determined by a person skilled in the art and may vary according to factors such as the disease state, age, sex, and weight of the individual, and the ability of the peptide to elicit a desired response in the individual. A therapeutically effective amount is also one in which any toxic or detrimental effects of the peptide are outweighed by the therapeutically beneficial effects. A therapeutically effective amount also encompasses an amount that is effective, at dosages and for periods of time necessary, to achieve the desired prophylactic (i.e., preventative) or therapeutic result.

In an aspect, the HPA3NT3 peptide may be admixed with at least one pharmaceutically acceptable carrier, diluent or excipient. As used herein, "pharmaceutically acceptable carrier, diluent or excipient" includes any and all solvents, dispersion media, coatings, isotonic and absorption delaying agents, and the like that are physiologically compatible. Examples of pharmaceutically acceptable carriers, diluents and excipients include but are not limited to one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride. Pharmaceutically acceptable carriers may further comprise minor amounts of auxiliary substances such as wetting or emulsifying agents, preservatives or buffers, which enhance the shelf life or effectiveness of the HPA3NT3 peptide.

It should be understood that the HPA3NT3 peptide may be formulated to be compatible with its intended route of administration, whether the route is parenteral, intravenous, intradermal, subcutaneous, oral, intranasal (e.g., inhalation), transdermal (e.g., topical), transmucosal, trans-tympanic, intratympanic, rectal administration or another accepted route of administration. Formulations of the HPA3NT3 peptide are formulated in accordance with routine procedures to prepare a pharmaceutical composition adapted for intravenous, subcutaneous, intramuscular, intraganglionic, oral, intranasal, intra-aural or topical administration to human beings and other animals, such as live stock and companion animals. For example, the HPA3NT3 peptide may be included in a composition for intravenous or intratympanic/trans-tympanic administration that may be a solution in sterile isotonic aqueous buffer. Moreover, in some aspects, the HPA3NT3 peptide may be formulated for administration via injection, such as an intradermal injection.

In some aspects, the HPA3NT3 peptide may be administered to a subject (e.g., an animal, such as human) as a portion of a topical composition. The topical composition may be manufactured as at least one of a liquid solution, a semi-solid solution, a cream, an ointment, a gel, or the like. For example, the topical composition may be formulated to be applied to the skin, the hair, or topical areas of the subject. Moreover, in some aspects, the topical composition may be formulated as a solution to be administered to one or both eyes of the subject. For example, the topical composition is formulated as eye drops for administration to one or both eyes of the subject.

As previously mentioned, some aspects of the invention include administering a therapeutically effective amount of the HPA3NT3 peptide to treat an infection. In one aspect, the therapeutically effective amount of HPA3NT3 peptide may be administered to a subject to treat a bacterial infection. For example, the bacterial infection may be the result of a colonization or attempted colonization by either a commensal organism or a non-commensal and/or pathogenic organism. In some aspects, the bacterial infection may be caused by Gram-positive bacteria and/or Gram-negative bacteria. In some aspects, the HPA3NT3 peptide may be used as a treatment to reduce or eliminate an infection associated with the skin of the subject. For example, the infection may be associated with any portion of the integumentary system of an animal (e.g., the epidermis, the dermis, the hypodermis, one or more hair follicles, one or more sebaceous glands, or any other area associated with the skin). In other words, the infection may be cutaneous in nature. Moreover, in some aspects, the infection may be associated with any other portion of the animal, such as portions of the vision system (e.g., the eyes) or the auditory system (e.g., portions of the ear, such as the tympanic cavity or portions of the auditory system positioned within the tympanic cavity).

In some aspects, the HPA3NT3 peptide is used in treating any one of a plurality of bacterial infections of an animal. In one aspect, the HPA3NT3 peptide may be administered to animals that are experiencing an overgrowth of one or more commensal organisms that are generally non-pathogenic or even beneficial for the animal. Some of these commensal bacteria may be from the following genre: *Staphylococcus, Mycobacterium*, and *Propionibacterium*. Moreover, other bacterial infections may result from the presence of known pathogens, such as bacteria from the genus *Pseudomonas*.

The following two bacteria are examples of bacterial infections that may be treated using one or more administrations of therapeutically effective amounts of HPA3NT3 peptide (as discussed in greater detail below).

Propionibacterium acnes

*Propionibacterium acnes* (*P. acnes*) is a ubiquitous gram-positive bacterium of that is generally considered to be a constituent of normal human skin microflora. As a general matter, *P. acnes* is present in high numbers in pilosebaceous follicles of individuals suffering from acne vulgaris. Torchia D et al., Segmental Acne Versus Mosaic Conditions with Acne Lesions, 224 DERMATOLOGY 10-14 (2012); Williams H C et al., Acne Vulgaris, 379 LANCET 361-72 (2012). This overabundance of *P. acnes* is generally associated with acne vulgaris, which is one of the most common disorders of human skin and affects nearly 50 million individuals in the United States alone. Acne vulgaris has many different symptoms including comedones, papules, pustules, nodules, cysts, and pilosebaceous inflammation. Del Rosso, J., Emerging Topical Antimicrobial Options for Mild-to-Moderate Acne: A Review of the Clinical Evidence, 7 J. DRUGS DERMATOL s2-s7. Moreover, acne vulgaris is a multifactorial inflammatory disease that results in significant scaring and disfigurement of the face and upper trunk of the individual. Del Rosso, J., Emerging Topical Antimicrobial Options for Mild-to-Moderate Acne: A Review of the Clinical Evidence, 7 J. DRUGS DERMATOL s2-s7.

The reduction of the numbers of *P. acnes* present on the skin and in the follicles of an infected individual generally correlates with clinical improvement. Thiboutot, D. M., Overview of Acne and Its Treatment, 81 CUTIS 3-7 (2008). Conventional treatments of acne vulgaris and *P. acnes* include antibiotics, such as oral tetracycline, topical erythromycin, and clindamycin; however these treatments have led to an increase in drug-resistant *P. acnes*, which has increased the incidence of therapeutic failure. Ghali, F., et al., Changing the Face of Acne Therapy, 83 CUTIS 4-15 (2009); and Tzellos T. et al., Treating Acne with Antibiotic-resistant Bacterial Colonization, 12 EXPERT OPINION ON PHARMACOTHERAPY 1233-1247 (2011). Moreover, additional conventional therapies include the use of benzoyl peroxide (BPO), which is a lipophilic non-antibiotic antibacterial agent; however BPO has a relatively high minimal inhibitory concentration (MIC) of 150 μg/mL, which makes BPO less effective relative to other treatments with a lesser MIC. Dhawan, S. S., Comparison of 2 Clindamycin 1%-Benzoyl Peroxide 5% Topical Gels Used Once Daily in the Management of Acne Vulgaris, 83 CUTIS 265-272 (2009); Del Rosso, J. Q., and G. Kim., Optimizing Use of Oral Antibiotics in Acne Vulgaris, 27 DERMATOL CLIN 33-42 (2009); and Tzellos T. et al., Treating Acne with Antibiotic-Resistant Bacterial Colonization, 12 EXPERT OPINION ON PHARMACOTHERAPY 1233-1247 (2011). Other conventional treatments include a 5% dapsone gel, which is a synthetic sulfone that has some potential for treatment of acne vulgaris; however the use of dapsone is limited by its high toxicity. Pickert, A., and S. Raimer, An Evaluation of Dapsone Gel 5% in the Treatment of Acne Vulgaris, 10 EXPERT OPIN PHARMACOTHER 1515-1521 (2009); and Stotland, M. et al., Dapsone 5% Gel: A Review of Its Efficacy and Safety in the Treatment of Acne Vulgaris, 10 AM J CLIN DERMATOL 221-227 (2009). Other conventional treatments exist, but suffer from similar shortcomings. See Charakida, A. et al., Safety and Side Effects of the Acne Drug, Oral Isotretinoin, 3 EXPERT OPIN DRUG SAF 119-129 (2004); and Dispenza M. C. et al., Systemic Isotretinoin Therapy Normalizes Exaggerated TLR-2-Mediated Innate Immune Responses in Acne Patients, 132 THE JOURNAL OF INVESTIGATIVE DERMATOLOGY 2198-2205 (2012).

*Pseudomonas aeruginosa*

*Pseudomonas aeruginosa* (*P. aeruginosa*) is a Gram-negative pathogen that may cause invasive and toxigenic infections affecting any portion of an individual (e.g., an animal, such as a human), including the respiratory system, the urinary system, the gastrointestinal tract, the central nervous system, as well as the blood, the heart, and the skeletal system. When present in the eyes and ears of an individual, *P. aeruginosa* may cause bacterial keratitis, scleral abscess, and endophthalmitis in adults and ophthalmia neonatorum and tympanitis in children. Moreover, *P. aeruginosa* infections in the skin may lead to lesions of ecthyma gangrenosum. In particular, the incidence of pseudomonal/bacterial keratitis has greatly increased with the advent and increased use of corrective contact lenses. Specifically, 25,000 contact lens wearers experience pseudomonal keratitis in the U.S. alone. In addition, the Centers for Disease Control estimates that the overall prevalence of *P. aeruginosa* infections in U.S. hospitals is approximately 4 per 1000 discharges.

Although most *P. aeruginosa* infections are treatable, growing resistance of this organism to antibiotics has complicated the efficacy of therapy and underscores the need for antibiotics with new mechanisms of action to treat multi-drug resistant *P. aeruginosa*. For example, the National Nosocomial Infection Surveillance System has reported resistance rates among *P. aeruginosa* isolates to imipenem and quinolones at 21.1% and 29.5%, respectively. National Nosocomial Infections Surveillance (NNIS) System Report, data summary from January 1992 through June 2004, issued October 2004 32 AM J INFECT CONTROL 470-485 (2004). The respective rates of resistance in isolates from intensive care units (ICUs) were even higher, up to 51.6% for ciprofloxacin, 31.4% for piperacillin/tazobactam, 38% for imipenem, and 23.6% for ceftazidime. Furthermore, relevant figures for ICU isolates of *P. aeruginosa* derived in Europe are even worse where resistance to aminoglycosides has reached 37-70%, to ceftazidime 57%, to piperacillin/tazobactam 53%, to ciprofloxacin 56%, and to imipenem 52%. Rossolini, G. M., and E. Mantengoli, Treatment and Control of Severe Infections Caused by Multiresistant Pseudomonas Aeruginosa, 11 CLIN MICROBIOL INFECT Suppl 4:17-32 (2005). With antibiotic resistance increasing at such a quick rate, it becomes necessary to investigate the consequences of sustained antibiotic exposure. Furthermore, hospital-acquired infection with *P. aeruginosa*, in particular, is often antibiotic-resistant, complicating the efficacy of therapy.

Anti-pseudomonal antibiotics are classified on the basis of their chemical structures as 1) beta-lactams, 2) quinolones, and 3) aminoglycosides. These drugs are capable of blocking invasive and toxigenic *P. aeruginosa* infections through one of three primary mechanisms of action: 1) interference with protein synthesis, 2) inhibition of cell wall synthesis, and 3) interference with nucleic acid replication.

Beta-lactam antibiotics are among the most widely prescribed agents in the U.S. and include piperacillin, ticarcillin, third- and fourth-generation cephalosporins (ceftazidime and cefepime, respectively), and carbapenems (e.g., imipenem or meropenem). Their bactericidal mechanism is interference with the synthesis of peptidoglycan, a major bacterial cell wall component, by binding to transpeptidases, also known as penicillin-binding proteins (PBPs). *P. aeruginosa* becomes resistant to beta-lactams by either producing enzymes, beta-lactamases, that hydrolyze the beta-lactam ring or altering PBPs so that they no longer bind and exert their effects. Moore, N. M., and M. L. Flaws, Treatment Strategies and Recommendations for Pseudomonas Aeruginosa Infections, 24 CLIN LAB SCI 52-56 (2011). The second classes of drugs used against *P. aeruginosa* are quinolones and fluoroquinolones (ciprofloxacin, levofloxacin, and ofloxacin). These agents interfere with DNA replication by inhibiting the activity of DNA gyrase and topoisomerase IV of *P. aeruginosa*. There are three major mechanisms of pseudomonal resistance to quinolones: 1) efflux pumps that decrease the intracellular concentration of the quinolone, 2) plasmid-encoded resistance genes that produce binding proteins to DNA gyrase, and 3) mutations in DNA gyrase or topoisomerase IV that decrease their binding affinity to quinolones, decreasing a drug's effectiveness. Moore, N. M., and M. L. Flaws, Treatment Strategies and Recommendations for Pseudomonas Aeruginosa Infections, 24 CLIN LAB SCI 52-56 (2011). The aminoglycosides (tobramycin, amikacin, and gentamicin), derived from *Streptomyces* species, inhibit protein synthesis by binding to either the 30 s or 50 s ribosomal subunit. Pseudomonal resistance to the aminoglycosides derives from enzymes that degrade the aminoglycosides or from active pumping of the drug out of the cell. Moore, N. M., and M. L. Flaws, Treatment Strategies and Recommendations for Pseudomonas Aeruginosa Infections, 24 CLIN LAB SCI 52-56 (2011); and Rossolini, G. M., and E. Mantengoli, Treatment and Control of Severe Infections Caused by Multiresistant Pseudomonas Aeruginosa, 11 CLIN MICROBIOL INFECT Suppl 4:17-32 (2005). These diverse mechanisms of antibiotic resistance acquired by *P. aeruginosa* underscore the need for new antibiotics with novel mechanisms of action to treat multidrug-resistant pseudomonal infections.

In some aspects, the therapeutically effective amount of HPA3NT3 peptide may be administered to a subject to treat an infection caused by non-bacterial organisms. In one aspect, the HPA3NT3 peptide may be administered to a subject to treat a fungal infection caused by one or more types of fungus (e.g., yeast). By way of example only, in some aspects, the HPA3NT3 peptide is administered to a subject to treat an infection caused by *Malassezia furfur*.

In particular, *M. furfur* is a commensal organism and an opportunistic pathogen that may cause cutaneous disorders, such as dandruff, seborrheic dermatitis, pityriasis versicolor, and folliculitis. In addition, under some circumstances, *M. furfur* may cause systemic disease associated with lipid-rich hyperlamination fluids. *M furfur*, which is a lipophilic, dimorphic fungus that may be found on and within human integumentary system. Generally, the treatment for *M. furfur* related-skin diseases is intended to control *M. furfur*-growth and the inflammation associated with its presence, as well as prevent secondary infections because the difficulty associated with treatment of *M. furfur* is the required prolonged use of medications and other treatments. Gaitanis G. et al., The Range of Molecular Methods for Typing Malassezia, 22 CURR. OPIN. INF. DIS. 119-125 (2009); and Gupta A. et al., Role of Antifungal Agents in the Treatment of Seborrheic Dermatitis, 5 AM. J. CLIN. DERMATOL. 417-422 (2004). However, medications available to treat these pathologies are both highly toxic and expensive when used as prolonged treatments. Liss, R. H. & F. R. Batchelor, Economic Evaluations of Economic Use and Resistance—A Perspective: A Report of Task Force 6, Supp. 3 REV. INFECT. DIS. s297-312 (1987). Moreover, finding an effective antifungal treatment that is non-cytotoxic to mammalian cells is especially challenging because both fungal cells and mammalian cells are eukaryotic in nature.

In some aspects, the HPA3NT3 peptide functions to treat infections in a manner substantially similar to other known antimicrobial peptides. Many antimicrobial peptides are able to permeabilize bacterial cell membranes in order to physically disrupt and directly kill target bacteria and fungi. Kim, S. S. et al., Antibacterial and Anti-inflammatory Effects of Jeju Medicinal Plants Against Acne-inducing Bacteria, 54 J GEN APPS MICROBIOL 101-106 (2008); Lee, D. Y. et al., Sebocytes Express Functional Cathelicidin Antimicrobial Peptides and Can Act to Kill Propionibacterium Acnes, 128 J INVEST DERMATOL 1863-1866 (2008); and Lai, Y., and R. L. Gallo, AMPed up Immunity: How Antimicrobial Peptides Have Multiple Roles in Immune Defense, 30 TRENDS IMMUNOL 131-141 (2009). In particular, at least a portion of the HPA3NT3 peptide includes an amphiphilic helical-shaped structure. Putsep, K., Antibacterial Peptide from *H. Pylori*, 398 NATURE 671-672 (1999). It is believed that the mechanism of action of the HPA3NT3 peptide is associated with the amphiphilic structure and its capacity to disrupt the lipid components of the infective agent's cell membrane.

Some aspects of the invention encompass administering a therapeutically effective amount of the HPA3NT3 peptide to reduce and/or treat inflammation. As used herein, the term "inflammation" is defined as a physiological response that occurs within vascularized tissue that is signified by the presence of one or more of the following indicators/symptoms: erythema, swelling, the induction of one or more "pro-inflammatory cytokines" at the transcriptional and/or translational levels, the induction of one or more intracellular signaling pathways that are known to be associated with inflammation, the presence and/or induction of cell membrane-associated receptors, the presence of cell infiltrate within the vascularized tissue, or other symptoms and indicia known by those skilled in the art to be associated with the presence of inflammation.

Moreover, as used herein, the term "pro-inflammatory cytokines" includes cytokines commonly associated with inflammation, including, but not limited to tumor necrosis factor alpha (TNF-$\alpha$), Interleukin-8 (IL-8), IL-1, and IL-6. In addition, as used herein, the term "intracellular signaling pathways" includes signal transduction pathways commonly associated with inflammation, including but not limited to nuclear factor kappa B (NF-$\kappa$B) and activator protein 1 (AP-1). Furthermore, as used herein, the term "cell membrane-associated receptors" includes, but is not limited to one or more pattern recognition receptors, such as members of the Toll-like Receptor (TLR) family, including TLR2 and TLR4.

In some aspects, the reduction and/or treatment of inflammation with a therapeutically effective amount of the HPA3NT3 peptide results in the reduction of at least some of the aforementioned symptoms/indicators associated with inflammation. In some aspects, the HPA3NT3 peptide may be administered to an animal (e.g., a human) that is experiencing one or more of the aforementioned symptoms/indicators such that the therapeutically effective amount of the HPA3NT3 peptide will reduce or treat at least some of the symptoms/indicators. For example, the induction of one or more pro-inflammatory cytokines as a result of an infection may be reduced or eliminated by the administration of a therapeutically effective amount of the HPA3NT3 peptide. In addition, as previously mentioned, the occurrence of inflammation may be the result of an infection (e.g., a bacterial or fungal infection) and/or physical damage to one or more tissues of the animal.

Some aspects of the invention encompass treating an infection and infection-induced inflammation in non-immortalized cells by administering a therapeutically effective amount of the HPA3NT3 peptide. As used herein "non-immortalized cells" refers to any cell types (either in vitro or in vivo) that do not proliferate indefinitely either through human intervention or a disease state, such as cancer. For example, non-immortalized cells include primary cells such as keratinocytes, dermal microvascular endothelial cells, corneal epithelial cells, and dermal fibroblasts.

METHODS AND EXAMPLES

All patents and publications mentioned throughout the specification are indicative of the levels of those skilled in the art to which the present disclosure pertains. All patents and publications are herein incorporated by reference to the same extent as if each individual publication was specifically and individually indicated to be incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that the use of such terms and expressions exclude any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

METHODS

Reagents and Cells

*P. acnes* (ATCC11828 and ATCC6919: American Type Culture Collection, Manassas, Va.) was cultured in Reinforced Clostridial Medium (BD: Franklin Lakes, N.J.) under anaerobic conditions using Gas-Pak at 37° C., then harvested by centrifugation at 2,000×g for 10 minutes at 4° C., and suspended in starvation medium at $1\times10^8$ colony forming units (CFU)/ml. Starvation medium was prepared using supplemented growth medium without hydrocortisone and bovine pituitary extract. Normal human keratinocytes (HK cells) (i.e., one form of non-immortalized/primary cells) from foreskin were purchased from PromoCell (Heidelberg, Germany) and cultured in supplemented keratinocyte growth medium at 37° C. with 5% $CO_2$. Cultured HK cells with 70% confluence were infected with *P. acnes*, and then subsequently incubated for the recited time periods, as described in greater detail below. Following infection with *P. acnes*, various concentrations (0.8, 1.6, or 3.2 μM) of the HPA3NT3 peptide or the HPN3 peptide were added to each well. Non-treated HK cells or HPN3-treated HK cells served as a negative control. HP(2-20) peptide and its analogues, including the HPA3NT3 and HPN3 peptides were synthesized as previously described in Park, H. K. et al., Influence of the N- and C-terminal Regions of Leu-Lys Rich Antimicrobial Peptide on Antimicrobial Activity, 15 PROTEIN PEPT LETT 188-192 (2008).

MIC Test by Microdilution Assays

*P. acnes* was suspended in the above-described liquid media and incubated until the population reached approximately $1\times10^8$ CFU/ml. Then, two-fold serial dilutions of the peptides (i.e., HP(2-20), HPANT3, and HPN3) (0.39 to 100 μM), clindamycin, or benzoyl peroxide (BPO) were plated into sterile 96-well microtiter plates. The suspension of *P. acnes* was then added to each well and the microtiter plates were incubated overnight at 37° C. under anaerobic conditions. The *P. acnes* plus peptide suspension was collected from the wells of the microtiter plates and aliquoted. Individual aliquots were then plated onto agar plates and incubated at 37° C. for 1 to 2 days. Colony counts were obtained at the end of the incubation period. The minimum inhibitory concentration (MIC) was defined as the lowest concentration of peptide that gave no visible growth on agar plates as described in Andrews J M, Determination of Minimum Inhibitory Concentrations, 48 J ANTIMICROB CHEMOTHER SUPPL 1:5-16 (2001).

Similar methods were used to determine the MIC of the HPA3NT3 peptide on *P. aeruginosa*. In brief, the MIC of the HPA3NT3 peptide and other antimicrobial peptides, as discussed below, on *P. aeruginosa* was determined using the same microdilution method discussed above using 96-well microtiter cell culture plates. *P. aeruginosa* (strain ATCC19660) was suspended in its liquid media to a concentration of $2\times10^4$ CFU/mL. Next, two-fold serial dilutions of each antimicrobial peptide (0.78 to 12.5 μM) were plated into sterile 96-well microtiter plates. The suspension of *P. aeruginosa* was then added to each well and the microtiter plates were incubated overnight (16 to 18 hours) at 37° C. under aerobic conditions. The *P. aeruginosa* and antimicrobial peptide suspensions were collected from the wells and aliquoted. Individual aliquots were then plated onto agar plates and incubated at 37° C. for 1 to 2 days. Colony counts were obtained at the end of the incubation period. The MIC was defined as the lowest concentration of peptide that gave no visible growth on agar plates as described in Andrews J M, Determination of Minimum Inhibitory Concentrations, 48 J ANTIMICROB CHEMOTHER SUPPL 1:5-16 (2001).

Similar methods were used to assess the MIC of antimicrobial peptides in *P. aeruginosa* derived from patient specimens (Patient #1 and Patient #2 who suffered from tympanitis). These patient-derived specimens were suspended in liquid media to a concentration of $2\times10^4$ CFU/mL. Two-fold serial dilutions of the peptides (HPA3NT3, LL37, Melittin) and antibiotics (Ceftazidime, Tazocin, Vancomycin) (4 to 64 μg/ml) were plated into sterile 96-well microtiter plates. The suspension of *P. aeruginosa* was then added to each well and the microtiter plates were incubated overnight (16 to 18 hours) at 37° C. under aerobic conditions. The *P. aeruginosa* and antimicrobial peptides or antibiotics suspensions were collected from the wells and aliquoted. Individual aliquots were then plated onto agar plates and incubated at 37° C. for 1 to 2 days. Colony counts were obtained at the end of the incubation period. The MIC was defined as the lowest concentration of peptide that gave no visible growth on agar plates as described in Andrews J M, Determination of Minimum Inhibitory Concentrations, 48 J ANTIMICROB CHEMOTHER SUPPL 1:5-16 (2001).

Similarly, *S. aureus* (strains ATCC8096, ATCC25923, or ATCC29213) was suspended in its liquid media to a concentration of $2\times10^6$ CFU/mL. Next, two-fold serial dilutions of each antimicrobial peptide (0.39 to 100 μM) were plated into sterile 96-well microtiter plates. Two-fold serial dilutions of clindamycin were used as a positive control (50 to 100 μM). The suspension of *S. aureus* was then added to each well and the microtiter plates were incubated overnight (16 to 18 hours) at 37° C. under aerobic conditions. The *S. aureus* and antimicrobial peptide suspensions were collected from the wells and aliquoted. Individual aliquots were then plated onto agar plates and incubated at 37° C. for 1 to 2 days. Colony counts were obtained at the end of the incubation period. The MIC was defined as the lowest concentration of peptide that gave no visible growth on agar plates as described in Andrews J M, Determination of Minimum Inhibitory Concentrations, 48 J ANTIMICROB CHEMOTHER SUPPL 1:5-16 (2001).

Similar methods were used to determine the MIC of the HPA3NT3 peptide on *M. furfur*. In brief, *M. furfur* was cultured at 32° C. on Sabouraud dextrose agar plates containing glycerol monostearate plus olive oil. Several colonies of *M. furfur* were collected from the agar plates and suspended in Sabouraud dextrose liquid media to a concentration of $4\times10^6$ CFU/mL. Two-fold serial dilutions of the HPA3NT3, HP(2-20), and HN3 peptides (0.2 to 100 μM) were prepared in Sabouraud dextrose liquid media and plated into sterile 96-well microtiter plates. The suspensions of *M. furfur* were then added to each well and the microtiter plates were incubated at 32° C. for 24 hours. The *M. furfur* plus peptide suspension was collected from the wells and aliquoted. Individual aliquots were then plated onto Sabouraud dextrose agar plates and incubated at 32° C. for 72 hours. Colony counts were obtained at the end of the incubation period. The MIC was defined as the lowest concentration of peptide that gave no visible growth on agar plates as described in Andrews J M, Determination of Minimum Inhibitory Concentrations, 48 J ANTIMICROB CHEMOTHER SUPPL 1:5-16 (2001).

Scanning Electron Microscopy (SEM) Analysis

*P. acnes* cells for SEM analysis were cultured as follows: *P. acnes* cells ($5\times10^5$) were cultured in the above-described culture medium and cells were washed within 10 mM sodium phosphate buffer (pH 5.5) 3 times with centrifugation steps at 4,000 rpm. Peptides (0.5×MIC, as determined above) (i.e., HP(2-20), HPA3NT3, and HPN3) were incubated with *P. acnes* cells at 37° C. in 10 mM sodium phosphate buffer (pH 5.5). After incubation, the bacteria were fixed in 4% glutaraldehyde for 20 min and dehydrated within 50 to 100% ethanol, with each specimen being incubated for 10 min at 37° C. All samples were coated onto gold particles and observations were made using a field emission-scanning electron microscopy (FE-SEM, JSM-7100F, Jeol, Japan).

MTT Assay

A conventional colorimetric assay for measuring the activity of MTT (yellow tetrazolium salt: 3-(4,5-dimethuylthiazol-2-yl)-2,5-diphenyltetrazolium bromide)-reducing enzymes was performed according to manufacturer's instruction (Molecular Probes, Inc., Eugene, Oreg.), using HK cells ($5\times10^3$ per 200 µl culture media) in the presence or absence of HPA3NT3 peptide or HPN3 peptide concentrations ranging from 1.6 to 6.4 µM. The data are expressed as the percentage of viable cells in comparison with that of 2% Triton X-100 treated control.

Determination of the Expression of IL-8 and TLR2 by Real-Time RT-PCR and Enzyme-Linked Immunosorbent Assay (ELISA)

HK cells were infected by *P. acnes* ATCC11828 ($1\times10^8$ CFU/ml) for 24 hours in the presence or absence of 3.2 µM HPA3NT3 peptide or HPN3 peptide. Total RNA was isolated using an RNeasy Mini Kit (Qiagen; Maryland, MD), then reverse transcribed to cDNA using MMLV reverse transcription kit (Promega; Madison, Wis.) according to the manufacturer's instructions. The mRNA expression of target genes was analyzed by real-time RT-PCR as described in the manufacturer's protocol (ABI 7500 real-time PCR system using SYBR Green master mix; Applied Biosystems, Foster City, Calif.). Oligonucleotide primers used to amplify human IL-8 and TLR2 cDNA were designed by the manufacturer's software (Primer Express 3.0; Applied Biosystems) based on the published sequences as described in Baggiolini M and Clark-Lewis I *Interleukin*-8, a chemotactic and inflammatory Cytokine, 307 FEBS LETTERS 97-101 (1992); and Rock F L et al., A family of human receptors structurally related to Drosophila Toll, 95 PROCEEDINGS OF THE NATIONAL ACADEMY OF SCIENCES OF THE UNITED STATES OF AMERICA 588-593 (1998). Target gene expression was normalized using an internal control gene 18S rRNA (Torczynski R M et al., Cloning and sequencing of a human 18S ribosomal RNA gene, 4 DNA 283-291 (1985)). The IL-8 primer sequences used were 5'-GCA GTT TTG CCA AGG AGT GCT-3' (SEQ. ID NO: 2) for the sense primer and 5'-TTT CTG TGT TGG CGC AGT GTG-3' (SEQ. ID NO: 3) for the antisense primer. The TLR2 primer sequences used were 5'-TGT CTT GTG ACC GCA ATG GT-3' (SEQ. ID NO: 4) for the sense primer and 5'-TGT TGG ACA GGT CAA GGC TTT-3' (SEQ. ID NO: 5) for the antisense primer. The 18S rRNA primer sequences used were 5'-CGG CTA CAT CCA AGG AA-3' (SEQ. ID NO: 6) for the sense primer and 5'-GCT GGA ATT ACC GCG GCT-3' (SEQ. ID NO: 7) for the antisense primer. To measure secreted IL-8 proteins, the collected HK cell supernatants were tested by ELISA using Quantikine human IL-8 immunoassay kit (R&D Systems, Minneapolis, Minn.) according to the manufacturer's instruction. All experiments were performed in triplicate.

A similar protocol was employed with *M. furfur*-infected cells. Specifically, HK cells were infected with *M. furfur* at a ratio of 27:1 (yeast to HK cell) for 24 hours, which was then followed by the addition of 0.2 µM HPA3NT3 peptide or negative control (HPN3). These experiments were repeated in serum-free media as well. Twenty-four hours after exposure to the peptides, supernatants and RNA were harvested and tested, as described above.

Determination of NF-κB Nuclear Translocation by Immunofluorescence Staining

Immunofluorescence analyses for NF-ϵB localization were performed as previously described in Song P I et al., The Expression of Functional CD14 and Toll-like Receptors on Human Keratinocytes, 117 THE JOURNAL OF INVESTIGATIVE DERMATOLOGY 438 (2001). Human keratinocytes were grown to about 70% confluence on chamber slides (No. 154526, Nalgene nunc, Rochester, N.Y.) and then treated with *P. acnes* for time periods ranging from 5 minutes to 1 hour in the presence or absence of 3.2 µM HPA3NT3 or HPN3 peptides. The cells were then incubated with rabbit anti-human NF-κB p65 polyclonal antibody (Rel A; Rockland, Gilbertsville, Pa.) diluted 1:3000 in blocking buffer (ImmPRESS kit; Vector Laboratories, Burlingame, Calif.), which was then followed by a 1 hour incubation with FITC-conjugated affinity-purified goat anti-rabbit IgG (H+L; Jackson ImmunoResearch Laboratories, INC., West Grove, Ga.), which was diluted 1:300 at room temperature in the dark. After washing, cells were incubated with TSA fluorescent reagent (Perkin Elmer, Boston, Mass.) for 30 minutes, then incubated with 1 µg/ml Hoechst 33342 (Invitrogen) for 30 minutes at room temperature. Dehydrated chamber slides were mounted and visualized with a microscope (Olympus EX51; Center Valley, Pa.).

A similar protocol was employed with *M. furfur*-infected cells. Specifically, HK cells at an about 70% confluence were infected with *M. furfur* at a ratio of 27:1 (yeast to HK cell) for 1 hour in the presence or absence of 0.2 µM HPA3NT3 peptide or negative control (HPN3). Thereafter, cells were fixed with 4% formaldehyde for 20 minutes at room temperature and incubated overnight with rabbit anti-human NF-κB p65 polyclonal antibody, which was dilued 1:3000 in blocking buffer with 0.1% Triton X-100 for permeabilization. Cells were then incubated with secondary anti-rabbit Ig HRP antibody for 1 hour. After washing, cells were incubated with TSA fluorescent reagent (Perkin Elmer, Boston, Mass.) for 30 minutes, then incubated with 1 µg/ml Hoechst 33342 (Invitrogen) for 30 minutes at room temperature. Dehydrated chamber slides were mounted and visualized with a microscope (Olympus EX51; Center Valley, Pa.).

Determination of TLR2 Cellular Localization by Immunofluorescence Staining

HK cells were cultured on chamber slides until it was determined that the concentration of these cells was about 70% confluent. Then, *P. acnes* was added to the chamber slides and incubated for 24 hours in the presence or absence of 3.2 µM HPA3NT3 or HPN3 peptides. HK cells were incubated overnight at 4° C. with rabbit anti-human TLR2 antibodies (Rockland, Gilbertsville, Pa.) diluted 1:3000 in buffer.

A similar protocol was employed with *M. furfur*-infected cells. Specifically, HK cells were infected with *M. furfur* at a ratio of 27:1 (yeast to HK cell) for 24 hours, which was in the presence or absence of 0.2 µM HPA3NT3 peptide or negative control (HPN3). HK cells were incubated overnight at at 4° C. with rabbit anti-human TLR2 antibodies (Rockland, Gilbertsville, Pa.) diluted 1:3000 in buffer.

Analysis of HK Intracellular Calcium Mobilization

HK cells were treated with *P. acnes* in the presence or absence of 3.2 µM HPA3NT3 or HPN3 during analyses of their fluorescence fluctuation, which was an indicator of intracellular calcium fluctuation, as measured using the following system. Intracellular calcium fluctuation was determined by InCyt Basic IM Fluorescence Imaging System (Intracellular Imaging INC, Cincinnati, Ohio) according to the manufacturer's instruction using 2 µM of the fluorescent calcium probe fura-2/acetylmethyl (AM) ester (Invitrogen, Carlsbad, Calif.).

A similar protocol was employed with *M. furfur*-infected cells. In brief, HK cells were grown on glass coverslips to approximately 50% to 70% confluence. Cells then were washed twice with PBS without $Ca^{2+}$ and $Mg^{2+}$, then incubated for 45 minutes at 37° C. in PBS containing 2 µM of the fluorescent calcium probe fura-2/acetylmethyl (AM) ester (Invitrogen, Carlsbad, Calif.). After three washes, cells were treated with *M. furfur* at a yeast cell to HK ratio of 27:1 in the presence or absence of 0.2 µM HPA3NT3 or HPN3 peptides during analyses of their fluorescence fluctuation.

*P. acnes*-Induced Inflammatory Response In Vivo

Right ears of ICR mice (Harlan, Indianapolis, Ind.) were intradermally injected with *P. acnes* ($1\times10^8$ CFU per 20 µl in Phosphate-Buffered Saline (PBS)) with or without HPA3NT3 peptide (6.4 µM). Left ears of the same mice were injected with 20 µl of PBS. In negative control ICR mice, right ears remained untreated while left ears received intradermal injections of PBS. For histological observation, the cross-sectioned ear was stained with hematoxylin and eosin (Sigma) and viewed on a Zeiss Axioskop2 plus microscope (Carl Zeiss) 24 to 48 hours after injection. The increase in ear thickness was measured using a micro caliper (Mitutoyo 547-400S; MSI Viking Gage, Charleston, S.C.) prior to, and at 24, 48, and 72 hours post injection. The percent difference in ear thickness (right vs. left ear) was determined by an induced ear inflammation ratio (percent difference in the experimental ear divided by the percent difference in the control ears). Ten milligrams of tissue from an 8 mm biopsy that was punched from ears at 24 hours after *P. acnes* injection was homogenized in 250 µl of sterile PBS with a tissue grinder. CFUs of *P. acnes* were determined by plating serial dilutions of the homogenate on an agar plate under anaerobic conditions for 48 hours.

Statistical Analysis

Statistical analysis results are expressed as mean±Standard Deviation. For statistical analysis, ANOVA with probabilities was performed for both the overall significance (p) and the pairwise comparison. $p<0.05$ was considered to be significant.

Determination of TLR4 and IL-8 Expression in *P. aeruginosa*-Infected Cells

Human corneal epithelial cells (HCET cells) were exposed to $2\times10^4$ CFU/mL tympanitis-derived *P. aeruginosa* either in the presence or absence of antimicrobial peptides. Specifically, HP(2-20) and its derivatives HPA3NT3, ISFGW, and F1AF8A were added to samples at concentration of 3.2 µM. Moreover, a cathilocidin-derived peptide (P5) was also added to some conditions at a concentration of 1.6 µM. After a 24 hour incubation, total RNA was isolated using an Rneasy Mini Kit (Qiagen; Maryland, MD), then reverse transcribed to cDNA using MMLV reverse transcription kit (Promega; Madison, Wis.) according to the manufacturer's instructions. The mRNA expression of target genes was analyzed by real-time RT-PCR as described in the manufacturer's protocol (ABI 7500 real-time PCR system using SYBR Green master mix; Applied Biosystems, Foster City, Calif.). Oligonucleotide primers used to amplify human IL-8 and TLR4 cDNA were designed by the manufacturer's software (Primer Express 3.0; Applied Biosystems).

EXAMPLES

HPA3NT3 Peptide has a Significantly Lower MIC Against *P. acnes* Compared to Benzoyl Peroxide To assess the bactericidal properties associated with some antimicrobial peptides, an experiment was performed to assess the minimum inhibitory concentration (MIC) of HP(2-20) and two of its derivative peptides, HPANT3 and HPN3, against two strains of *P. acnes* (ATCC11828 and ATCC6919). In particular, HPN3 was used as a negative control because it has been previously shown to exhibit a high MIC against *P. acnes*. In addition, benzoyl peroxide and clindamycin, two conventional treatments known to kill *P. acnes* were also included as controls. Referring to Table 1A, the MIC value of HP(2-20) and HPA3NT3 peptide were 0.8 and 0.4 µM, respectively, which is similar to that of clindamycin, a proven treatment against *P. acnes* infection. Moreover, the MIC value of HPA3NT3 peptide against *P. acnes* was 156 times lower than that of benzoyl peroxide (62.5 µM) and 32 times lower than the HPN3 peptide negative control (>12.8 µM). These results demonstrate the greater bactericidal activity of the HPA3NT3 peptide relative to other peptides and benzoyl peroxide.

TABLE 1A

| | MIC (µM) against *P. acnes* | |
|---|---|---|
| Treatments | ATCC11828 | ATCC6919 |
| HPA3NT3 | 0.4 | 0.4 |
| HPN3 (inactive control) | >12.8 | >12.8 |
| HP(2-20) | 0.8 | 0.8 |
| Clindamycin | <0.2 | <0.2 |
| Benzoyl Peroxide | 62.5 | 125 |

HPA3NT3 Peptide Also Exhibits a Lower MIC Against *M. furfur* Relative to Control Peptides To assess the fungicidal properties associated with some antimicrobial peptides, an experiment was performed to determine the minimum inhibitory concentration (MIC) of HP(2-20) and two of its derivative peptides, HPANT3 and HPN3, against *M. furfur*. In particular, the HPN3 peptide was used as a negative control. Referring to Table 1B, the MIC value of HP(2-20) and HPA3NT3 peptides were <0.195 and <0.09 µM, respectively, which is significantly less than the MIC of the HPN3 peptide (>50). These results demonstrate the significant fungicidal activity of the HPA3NT3 peptide and its parent peptide, HP(2-20).

TABLE 1B

| Treatments | MIC (µM) against *M. furfur* |
|---|---|
| HPA3NT3 | <0.09 |
| HPN3 (inactive control) | >50 |
| HP(2-20) | <0.195 |

HPA3NT3 Peptide Also Exhibits a Lower MIC Against *S. aureus* Relative to Control Peptides To assess the bactericidal properties associated with some antimicrobial peptides against *S. aureus*, an experiment was performed to determine the minimum inhibitory concentration (MIC) of HP(2-20) and two of its derivative peptides, HPANT3 and HPN3, as well as ISFGW and clindamycin against three strains of *S. aureus* (ATCC8096, ATCC25923, ATCC29213). Referring to Table 1C, depending on the strain of *S. aureus*, the MIC value of HP(2-20), ISFGW, HPA3NT3 peptides were generally less than the MIC of the HPN3 peptide and clindamycin (>50). These results demonstrate the significant bactericidal activity of the HPA3NT3 peptide against *S. aureus*, relative to the control treatments.

TABLE 1C

| Treatments | MIC (µM) against S. aureus | | |
|---|---|---|---|
| | ATCC8096 | ATCC25923 | ATCC29213 |
| HPA3NT3 | 3.13 | 50 | 25 |
| HPN3 | >50 | >50 | >50 |
| HP(2-20) | 6.25 | >50 | >50 |
| Clindamycin | >50 | >50 | >50 |
| ISFGW | 3.13 | 12.5 | 6.25 |

HPA3NT3 Peptide Exhibits a Lower MIC Against P. aeruginosa Relative to Control Peptides To assess the bactericidal properties associated with the HPA3NT3 peptide against P. aeruginosa, an experiment was performed to determine the minimum inhibitory concentration (MIC) of HP(2-20) and three of its derivative peptides, HPANT3, HPN3, and ISFGW-P-A3NT3. In addition, three other cathelicidin-based antimicrobial peptides, CA-MA, p4, and p5 were assessed as well to determine the respective MICs against one strain of P. aeruginosa (ATCC19660). Referring to Table 1D, the MIC value of HP(2-20), ISFGW, HPA3NT3 peptides were less than the MIC of the HPN3 peptide (>12.5) and at least one of the cathelicidin-based peptides (p4). These results demonstrate the significant bactericidal activity of the HPA3NT3 peptide against P. aeruginosa, relative to the control treatments.

TABLE 1D

| Treatments | MIC (µM) against P. aeruginosa (ATCC19660) |
|---|---|
| HPA3NT3 | 1.562 |
| HPN3 | >12.5 |
| HP(2-20) | 3.125 |
| ISFGW-P-A3NT3 | 1.562 |
| CA-MA | 1.562 |
| p4 | >12.5 |
| p5 | 0.78 |

A similar experiment was performed on clinically-derived isolates of P. aeruginosa. These particular isolates were derived from patients with tympanitis. In this experiment, three different antimicrobial peptides (HPA3NT3, LL37, and Melittin) and three different conventional antibiotic compositions (ceftazidime, tazocin, and vancomycin) were used to assess the different MICs. Referring to Table 1E, in general, the antimicrobial peptides exhibited lower MICs relative to the conventional antibiotic compositions. In particular, the HPA3NT3 peptide exhibited a lower MIC than the LL37 peptide and a similar level to Melittin, all of which were more effective (i.e., lower MIC levels) than the conventional antibiotics. Overall, the above-described data supports the conclusion that the HPA3NT3 peptide possesses bactericidal activity against both ATCC-deposited strains of P. aeruginosa, as well as clinical isolates of P. aeruginosa. In addition, the data in Table 1E further supports the conclusion that the HPA3NT3 peptide may be used against strains of P. aeruginosa that have previously acquired/developed resistance to one or more conventional antibiotics.

TABLE 1E

| Treatments | MIC (µg/mL) against P. aeruginosa | |
|---|---|---|
| | Patient #1 | Patient #2 |
| HPA3NT3 | 16 | 16 |
| LL37 | >32 | >32 |
| Melittin | 8 | 16 |
| Ceftazidime | >32 | >32 |
| Tazocin | 32 | >32 |
| Vancomycin | >32 | >32 |

HPA3NT3 Peptide Functions without Cytotoxicity to Human Keratinocytes

To determine cytotoxic effects of the peptides on primary human keratinocytes (HK cells) (i.e., non-immortalized cells), an experiment was conducted to measure HK cell-viability using an MTT assay 24 hours after treatments of HPA3NT3 peptide or HPN3 peptide, as shown in Table 1F. In particular, the percentages of HK cell-viability after treatment with 1.6, 3.2, and 6.4 µM of HPA3NT3 peptide or HPN3 peptide were 100%. In contrast, treatment with a 2% Triton X-100 solution (a detergent) results in less than 2% HK cell-viability.

TABLE 1F

| Concentration (µM) | HPA3NT3 (Cell viability in %) | HPN3 (Cell viability in %) | Triton X-100 (Cell viability in %) |
|---|---|---|---|
| 1.6 | 100 | 100 | <2 |
| 3.2 | 100 | 100 | — |
| 6.4 | 100 | 100 | — |

A similar experiment was carried out using HK cells in both a serum-free medium and a serum-containing medium, as shown in FIGS. 1A-1C. Specifically, HK cell viability was determined 24 hours after treatment with different concentrations of the HPA3NT3 peptide (1.6, 3.2, and 6.4 µM) relative to a negative control. Treatment with HPA3NT3 peptide induced only minimal cytotoxicity, even at the highest concentration of 6.4 µM under both serum-free and serum-containing conditions. The results from these experiments demonstrate that HPA3NT3 peptide does not have eukaryotic cell cytotoxicity that could interfere with the use of HPA3NT3 peptide as a therapeutic agent applied to the skin.

HPA3NT3 Peptide Induces the Morphological Perturbation and Blebs of P. acnes

Figure 2:
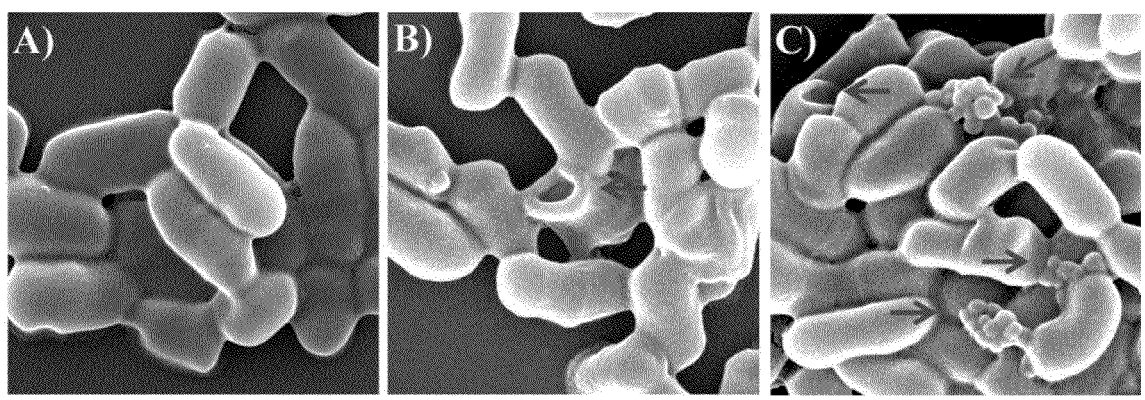
FIG. 2 depicts the morphological perturbation and blebs of *P. acnes* induced by treatments with a negative control (A), HP(2-20) peptide (B), or HPA3NT3 peptide (C), as visualized under 20,000× magnification at 15.0 kV. The arrows in this figure are aimed toward the morphological perturbations and bleb.

An experiment was performed to determine the impact of certain peptides on the morphology of P. acnes. The experiment investigated the impact of the HPA3NT3 and HP(2-20) peptides on the morphology of P. acnes, as viewed using scanning electron microscopy. Specifically, as shown in FIGS. 2A-2C, using only 50% of the MIC (as determined above), the HPANT3 peptide induced morphological perturbation and blebs of P. acnes cell walls (as highlighted by the arrows in FIG. 2C); however, using the same relative concentration of HP(2-20), only minimal morphological changes were noted in the cell wall (as shown in FIG. 2B). This difference may reflect the fact that HP(2-20) reaches the membrane predominantly in the form of monomers that aggregate on the surfaces of negatively-charged membranes once a threshold concentration has been reached, whereas HPA3NT3 molecules reach the membrane as highly-ordered oligomers, which would enable more efficient membrane perturbation. Regardless, the morphological perturbation and blebs are indicators that exposure of P. acnes to the HPA3NT3 peptide is leading to cell-membrane disruption.

Figure 3:
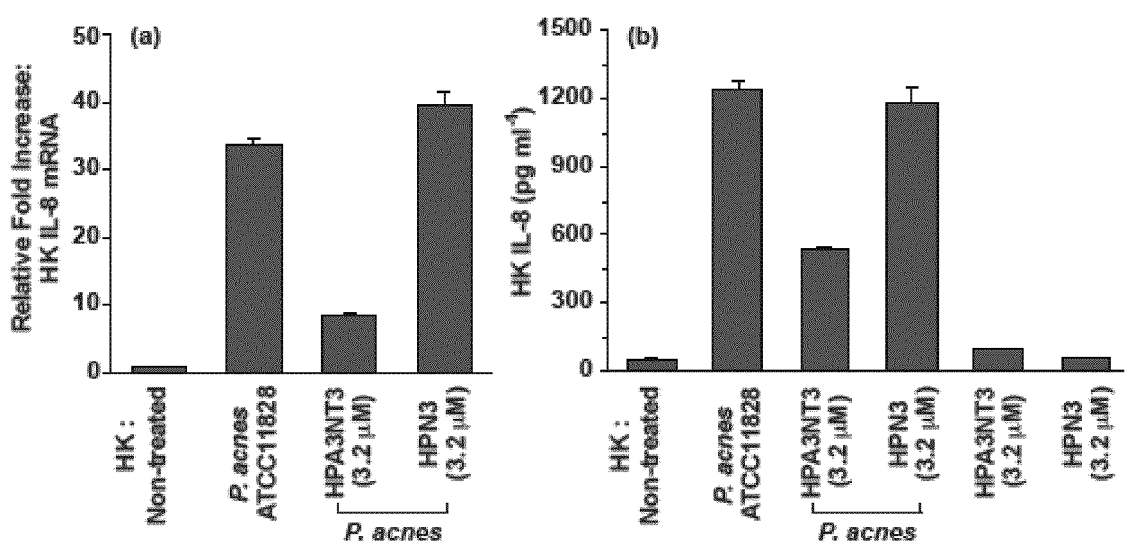
FIG. 3 graphically depicts HK cell IL-8 mRNA expression as measured by real-time RT-PCR (A) and the secretion of IL-8 protein as measured by ELISA (B) after infection with *P. acnes* and with or without HPA3NT3 peptide or HPN3 peptide. The data shown are representative of triplicate experiments. All values in these graphs are expressed as mean±standard deviation.

HPA3NT3 Peptide Inhibits the Expression of HK Cell IL-8 Induced by P. acnes Infection Interleukin-8 (IL-8) is a potent chemotactic cytokine that recruits neutrophils and lymphocytes to infection sites in the skin. Kim J., Review of the Innate Immune Response in Acne Vulgaris: Activation of Toll-like Receptor 2 in Acne Triggers Inflammatory Cytokine Responses, 211 DERMATOLOGY 193-198 (2005). An experiment was conducted to investigate the biological role of the peptides in vitro in the initiation of an innate inflammatory response induced by P. acnes infection. In particular, the expression of P. acnes-induced HK cell IL-8 mRNA and protein was measured via real-time RT-PCR and ELISA in the presence or absence of HPA3NT3 or HPN3 (negative control). As shown in FIG. 3A, IL-8 mRNA is increased 34 fold in HK cells as a result of P. acnes infection, which concurs with previously published data. Grange P. A. et al., Nicotinamide Inhibits Propionibacterium Acnes-induced IL-8 Production in Keratinocytes Through the NF-Kappa B and MAPK Pathways, 56 JOURNAL OF DERMATOLOGICAL SCIENCE 106-112 (2009). Interestingly, when the HK cells were treated with the HPA3NT3 peptide in addition to being exposed to P. acnes, IL-8 mRNA levels were significantly down-regulated (>85%) compared to HK cells that did not receive the HPA3NT3 peptide treatment. In contrast, P. acnes-infection induced IL-8 mRNA expression was not inhibited or reduced by the treatment with HPN3 peptide. As shown in FIG. 3B, treatment with the HPA3NT3 peptide significantly reduced (>55%) P. acnes-infection induced IL-8 protein secretion from the HK cells, as compared to the inhibition rate by treatment with HPN3 peptide (0%) 24 hours after treatment. Moreover, no significantly increased secretion of IL-8 protein was induced by the treatment with HPA3NT3 and HPN3 peptides alone. Accordingly, treatment with HPN3NT3 peptide functions to reduce and/or treat inflammation arising from P. acnes infection.

HPA3NT3 Peptide Inhibits P. acnes-Induced HK Cell NF-κB Nuclear Translocation

Figure 4:
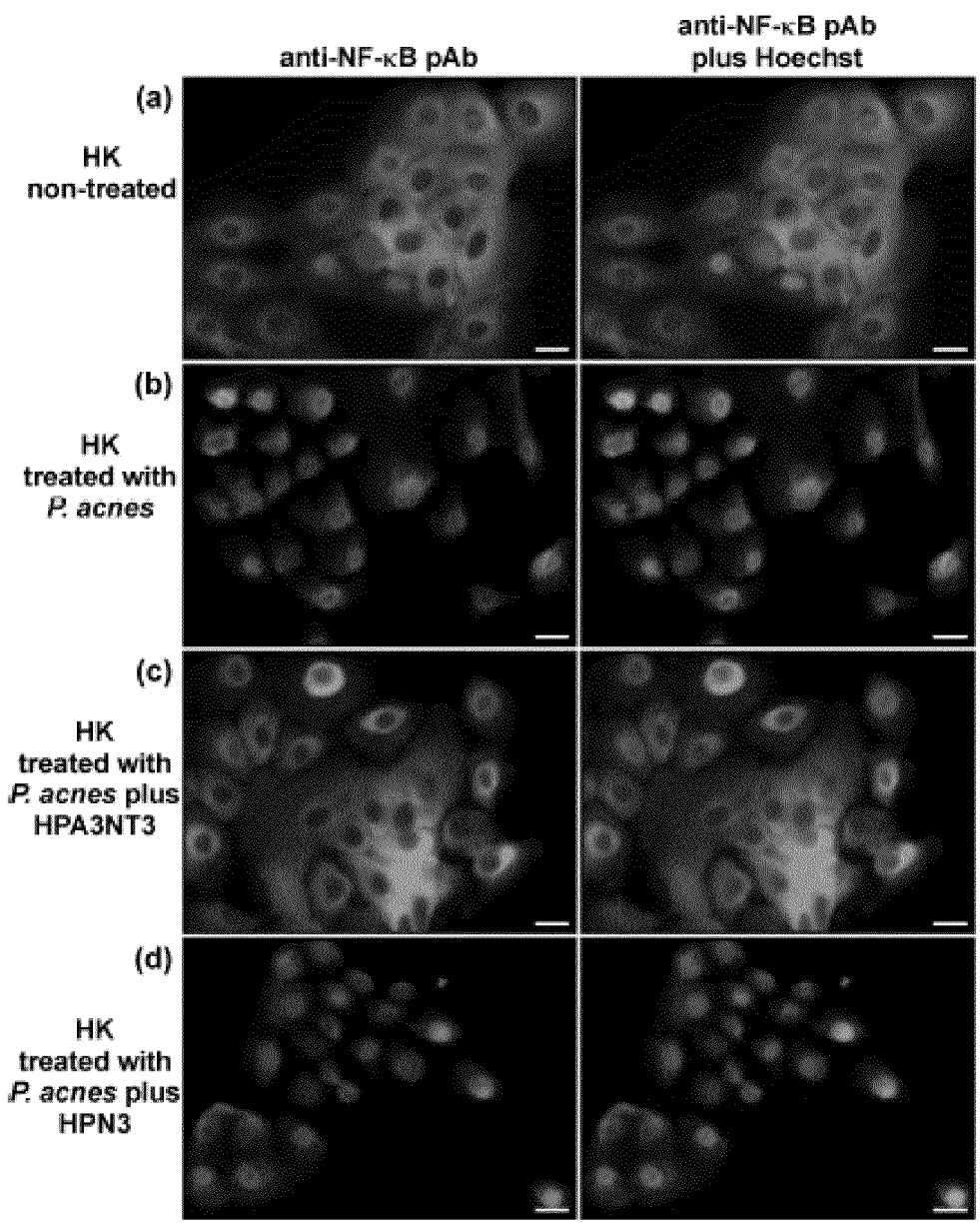
FIG. 4 depicts immunofluorescent staining of cellular NF-κB protein in HK cells that were uninfected (A), infected with $1 \times 10^8$ CFU/mL *P. acnes* for 30 minutes (B), infected with $1 \times 10^8$ CFU/mL *P. acnes* for 30 minutes and treated with 3.2 µM HPA3NT3 peptide (C), or infected with $1 \times 10^8$ CFU/mL *P. acnes* for 30 minutes and treated with 3.2 µM HPN3 peptide (D).

Nuclear factor-kappa B (NF-κB) plays a key role as a transcriptional regulator of multiple inflammation-related genes, including IL-8 and TNF-α. Pasparakis M., Role of NF-KappaB in Epithelial Biology, 246 IMMUNOLOGICAL REVIEWS 346-358 (2012). An experiment was performed to determine the role of the HPA3NT3 peptide in augmenting NF-κB-based responses in P. acnes-infected HK cells. Accordingly, the localization of intracellular NF-κB was determined by immunofluorescence staining using an anti-NF-κB p65 polyclonal antibody, with the results of this experiment shown in FIG. 4. Initially, in uninfected HK cells, the NF-κB p65 staining was primarily localized to the cytoplasm, as shown in FIG. 4A. However, nuclear translocation of NF-κB p65 was rapidly induced upon infection of the HK cells with P. acnes, as shown in FIG. 4B. Interesting, co-incubation of HK cells with both P. acnes and the HPA3NT3 peptide resulted in an effective blocking of P. acnes-induced NF-κB p65 nuclear translocation, as shown in FIG. 4C. In contrast, when the HK cells were co-incubated with P. acnes and the HPN3 peptide (the negative control), nuclear translocation of NF-κB p65 was not blocked, as shown in FIG. 4D. Accordingly, this data further demonstrates that treatment with the HPA3NT3 peptide works to suppress the natural processes carried out by cells to produce an inflammatory response to a stimulus, in this case, a P. acnes infection.

Figure 5:
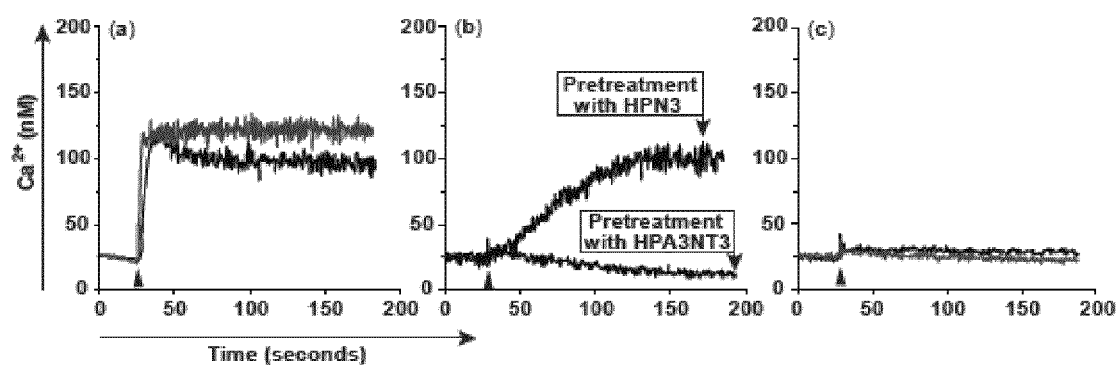
FIG. 5 depicts intracellular calcium fluctuations in HK cells that were infected with $1 \times 10^8$ CFU/150 µL *P. acnes* in the absence (A) or presence of 3.2 µM HPA3NT3 peptide or HPN3 peptide (B) or uninfected HK cells in the presence of 3.2 µM HPA3NT3 peptide of HPN3 peptide (C).

HPA3NT3 Peptide Abrogates HK Cell Intracellular Calcium Fluctuation Induced by P. acnes Infection It has been previously reported that unsaturated fatty acids derived from P. acnes affect calcium dynamics in epidermal keratinocytes, which results in a disruption of the skin barrier function and leads to abnormal keratinization. Katsuta Y. et al., Unsaturated Fatty Acids Induce Calcium Influx into Keratinocytes and Cause Abnormal Differentiation of Epidermis, 124 THE JOURNAL OF INVESTIGATIVE DERMATOLOGY 1008-1013 (2005). Accordingly, the role of the HPA3NT3 peptide was investigated in terms of its impact on intracellular calcium signaling. In this experiment, HK cells were pre-incubated with or without HPA3NT3 peptide and then infected with P. acnes. As shown in FIG. 5A, in HK cells that were not pre-treated with the HPA3NT3 peptide and infected with P. acnes, the infection resulted in a rapid intracellular calcium fluctuation. Conversely, as shown in FIG. 5B, pre-incubation with 3.2 µM HPA3NT3 peptide abrogated the P. acnes-infection induced intracellular calcium fluctuation. However, HK cells that were pre-incubated with the HPN3 peptide did not exhibit the abrogated intracellular calcium fluctuation noted in the HPA3NT3 peptide condition, as also shown in FIG. 5B. Stimulation with the two test peptides alone resulted in little intracellular calcium fluctuation, as shown in FIG. 5C. This data shows that the HPANT3 peptide efficiently blocks a rapid fluctuation of intracellular calcium that is induced by a P. acnes infection, which further supports the conclusion that this peptide has a functional competence in non-immortalized cells.

Figure 6:
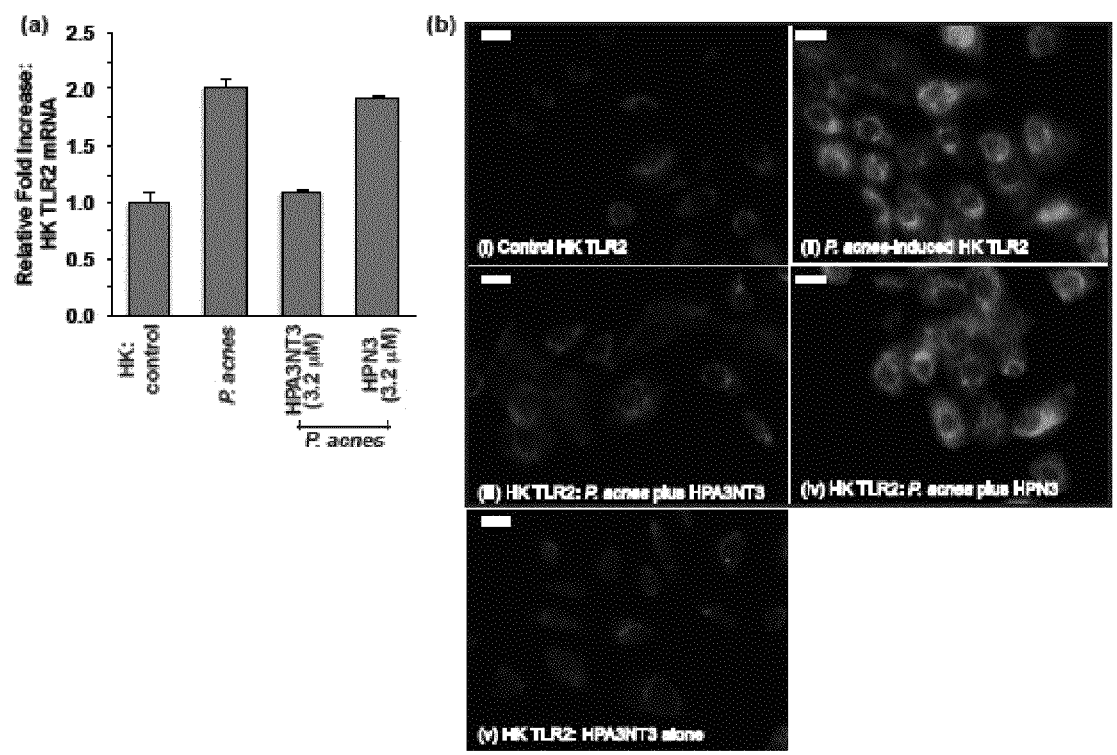
FIG. 6 depicts TLR2 mRNA expression as measured by real-time RT-PCR in HK cells after infection with *P. acnes* with or without HPA3NT3 peptide or HPN3 peptide (A). Localization of TLR2 protein was determined by immunofluorescent staining in HK cells (B) that were uninfected (i), infected with *P. acnes* (ii), infected with *P. acnes* plus HPA3NT3 peptide (iii), infected with *P. acnes* plus HPN3 peptide (iv), and HK cells treated with HPA3NT3 alone (v). The scale bar is equal to 20 µm.

HPA3NT3 Peptide Significantly Inhibits the Expression of HK Cell TLR2 Induced by P. acnes Infection Some research literature indicates that P. acnes contributes to inflammation in acne vulgaris through the activation of TLR2, which in turn leads to the production of pro-inflammatory cytokines such as IL-8 and TNF-α through the NF-κB signaling pathway. Kim J., Review of the Innate Immune Response in Acne Vulgaris: Activation of Toll-like Receptor 2 in Acne Triggers Inflammatory Cytokine Responses, 211 DERMATOLOGY 193-198 (2005). Accordingly, an experiment was conducted to examine the functional role of the HPA3NT3 peptide in augmenting the expression of TLR2 in HK cells that are infected by P. acnes. In short, HK cells were infected with P. acnes and treated with HPA3NT3 peptide, HPN3 peptide, or nothing and mRNA was analyzed 24 hours later. As illustrated by the graph in FIG. 6A, TLR2 mRNA was increased by two fold in HK cells 24 hours after P. acnes infection. In contrast, when HK cells were also treated with the HPA3NT3 peptide, the increase in TLR2 mRNA that resulted from the P. acnes infection was significantly down-regulated ($p<0.001$). However, this down-regulation was not seen in cells that were treated with the HPN3 peptide. Similarly, as shown in FIGS. 6B(i)-6B(iv), treatment with the HPA3NT3 peptide effectively inhibited P. acnes-induced cellular expression of TLR2 protein compared to the negative control peptide, HPN3. Moreover, treatment with HPA3NT3 and HPN3 peptides alone did not impact TLR2 protein levels. This data again supports the conclusion that HPA3NT2 peptide reduces and/or treats inflammation that is caused by P. acnes infection.

Figure 7:
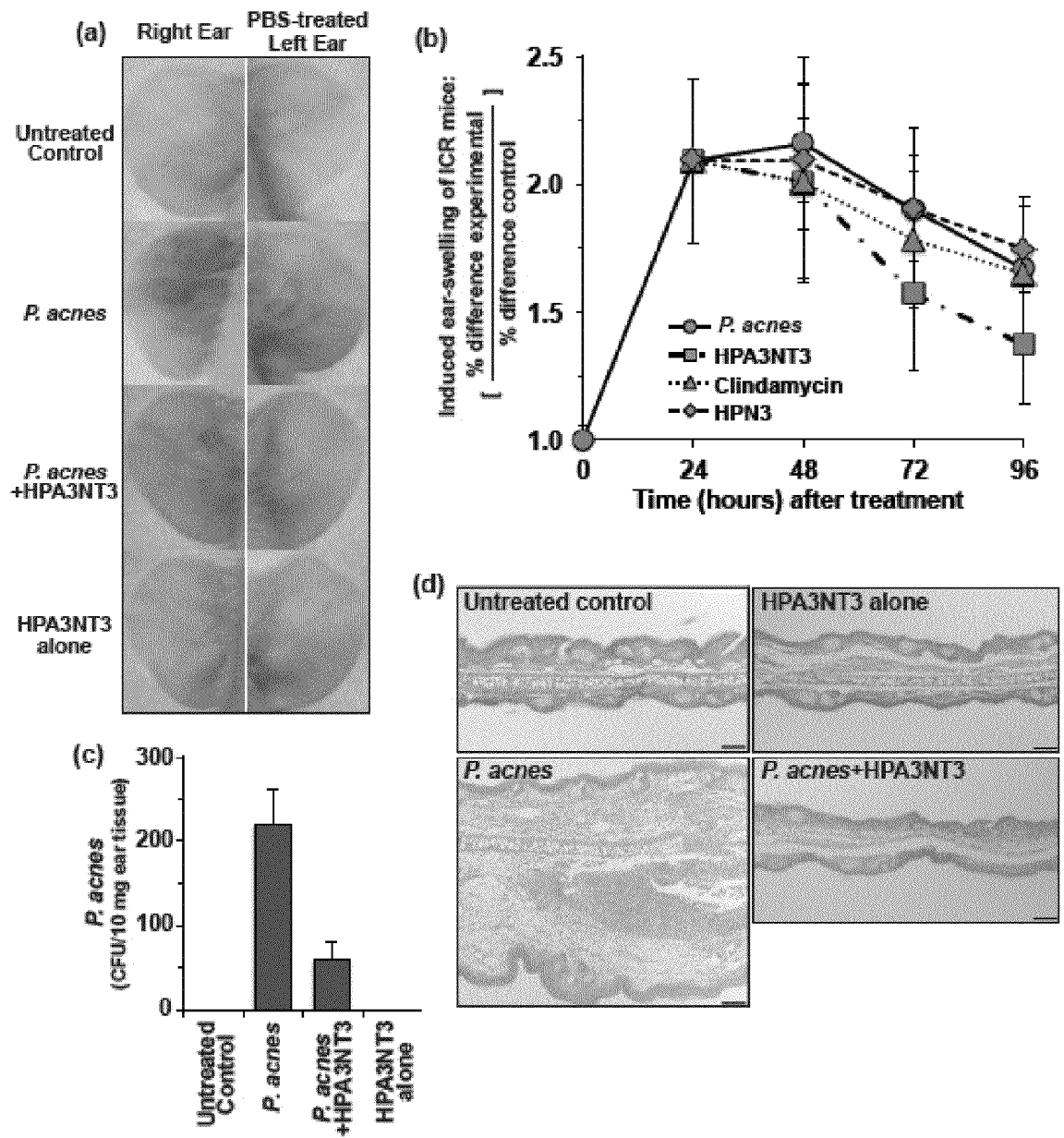
FIG. 7 depicts inflammation-induced erythema in ICR mouse ears 24 hours after injection (A) with *P. acnes*, *P. acnes* plus HPA3NT3 peptide, and HPA3NT3 peptide alone, and untreated ICR mouse ears as a negative control. This figure also includes the percent differences in ear swelling (B) and the number of *P. acnes* colonized within the ear of infected ICR mice (C). This figure also includes hematoxylin-and-eosin-stained paraffin embedded sections of ears (D). The scale bar is equal to 0.2 mm.

Intradermal Injection of HPA3NT3 Peptide at a P. acnes-Infected Site of ICR Mouse Ears Significantly Blocks P. acnes Growth and P. acnes-Induced Inflammatory Responses In Vivo In order to extend the above-described results to an in vivo setting, an experiment was performed to investigate the in vivo effects of the HPA3NT3 peptide on inflammatory responses using a P. acnes-injected ICR mouse ear model. As shown in FIGS. 7A and 7B, right ears of ICR mice that were injected with P. acnes exhibited cutaneous erythema (FIG. 7A) and ear swelling with granulomatous tissues (FIG. 7B) 24 to 48 hours post intradermal injection, as compared to PBS-injected control ears (i.e., the left ears) (FIG. 7A). When the HPA3NT3 peptide was administered in the *P. acnes*-infected ears, the treatment significantly reduced cutaneous erythema (FIG. 7A) and ear swelling (FIG. 7B), as well as the number of *P. acnes* colonized within the ear tissue (FIG. 7C). Moreover, when compared with clindamycin, a conventional treatment for *P. acnes*, treatment with HPA3NT3 peptide was more efficient at reducing ear swelling, as illustrated in FIG. 7B. Similar to previous experiments, the HPA3NT3 peptide was administered to uninfected ears, which produced no significant changes in erythema or ear swelling, as shown in FIGS. 7A and 7B.

The above data was further supported by the histological study of FIG. 7D. In particular, an experiment was conducted to examine the *P. acnes*-infection induced histological appearance of the inflammation process in the ears in the presence or absence of HPA3NT3 peptide. As shown in FIG. 7D, administration of the HPA3NT3 peptide significantly reduced *P. acnes*-induced mouse ear swelling and inflammatory infiltrate 24 hours after bacterial injection. Moreover, the HPA3NT3 peptide alone did not affect ear thickness or inflammation. Taken together, these results demonstrate that the administration of the HPA3NT3 peptide leads to significantly enhanced bactericidal activity and anti-inflammatory effects in vivo.

Figure 8:
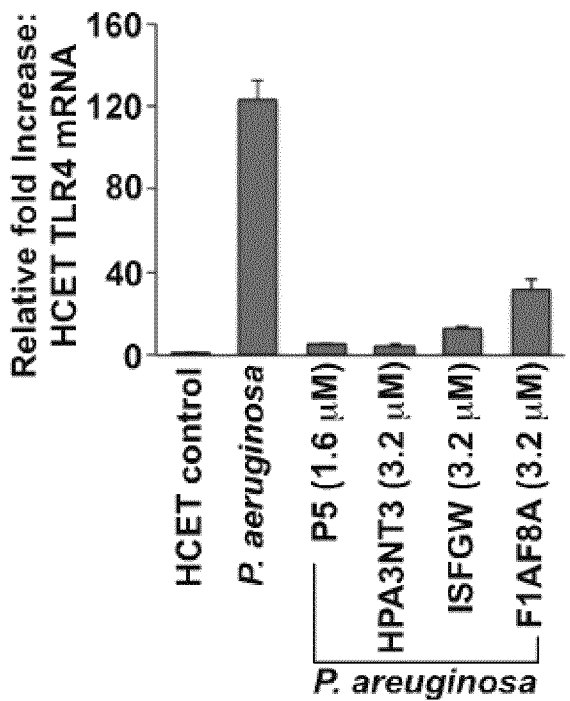
FIG. 8 graphically depicts the impact of HPA3NT3 on TLR4 mRNA levels in human corneal epithelial cells that have been infected with *P. aeruginosa*.

HPA3NT3 Peptide Inhibits TLR4 mRNA in Human Corneal Epithelial Cells that is Induced by *P. aeruginosa* Infection In order to also investigate the impact of HPA3NT3 peptide treatment on *P. aeruginosa* infection, an experiment was conducted to assess whether HPA3NT3 peptide similarly augments host inflammation during a *P. aeruginosa* infection. In this experiment human corneal epithelial cells (HCET cells) were exposed to $2\times10^4$ CFU/mL *P. aeruginosa* and then incubated with one of the following peptides: HPA3NT3 (3.2 μM), HPN3 (3.2 μM) ISFGW, an HP(2-20) analog (3.2 μM), F1AF8A, another HP(2-20) analog (3.2 μM), and P5, a cathelicidin analog (1.6 μM). After incubation, RNA was harvested and TLR4 transcriptional levels were assessed, with the data shown in FIG. 8. Initially, *P. aeruginosa* infection increased expression of TLR4 mRNA in HCET cells by over 120 fold compared to uninfected HCET cells. Conversely, treatment with the HPA3NT3 peptide significantly reduced the *P. aeruginosa*-infection induced increase in TLR4 mRNA to only an approximately 5-fold increase. Similar inhibition was seen with some of the other peptides. Moreover, use of the HPN3 peptide did not have an impact on TLR4 mRNA (data not shown). Accordingly, this data shows that the HPA3NT3 peptide likely has a impact on inflammation that is not only induced by *P. acnes*, but also other organisms, including *P. aeruginosa*.

Figure 9:
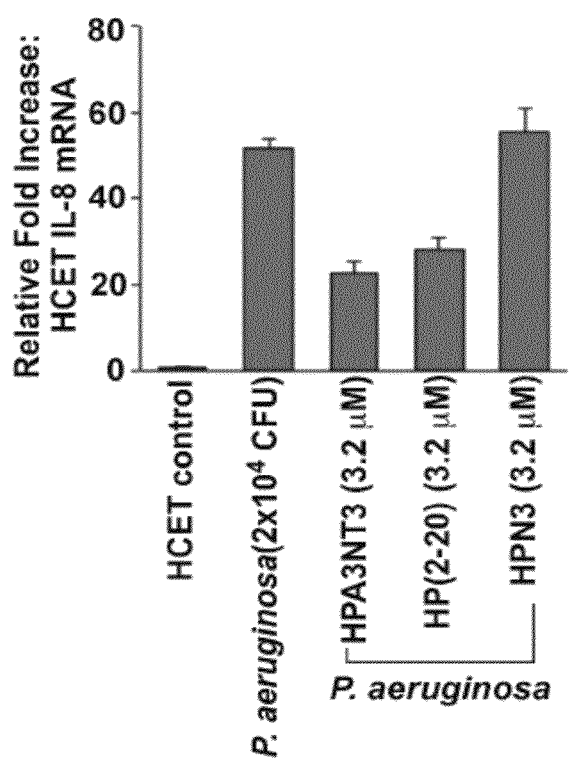
FIG. 9 graphically depicts the impact of HPA3NT3 on IL-8 mRNA levels in human corneal epithelial cells that have been infected with *P. aeruginosa*.

HPA3NT3 Peptide Inhibits IL-8 mRNA in Human Corneal Epithelial Cells that is Induced by *P. aeruginosa* Infection In this experiment HCET cells were exposed to $2\times10^8$ CFU/20 μL *P. aeruginosa* and then incubated with one of the following peptides: HPA3NT3 (3.2 μM), HPN3 (3.2 μM) or HP(2-20) (3.2 μM). After incubation, RNA was harvested and IL-8 transcriptional levels were assessed, with the data shown in FIG. 9. As expected, infection with *P. aeruginosa* significantly induced IL-8 expression in HCET cells and the negative control peptide, HPN3, did not augment this response. However, treatment with both the HPANT3 and HP(2-20) peptides significantly inhibited the *P. aeruginosa* infection induced IL-8 expression in HCET cells after 24 hours. Similar to the data above, administration of the HPA3NT3 peptide and HP(2-20) peptide without *P. aeruginosa* did not impact the expression of IL-8 in HCET cells (data not shown).

HPA3NT3 Peptide Inhibits IL-8 mRNA and Protein in HK Cells that is Induced by *M. furfur* Infection In order to also investigate the impact of HPA3NT3 peptide treatment on *M. furfur* infection, an experiment was conducted to assess whether HPA3NT3 peptide similarly augments host inflammation during a *M. furfur* infection. In this experiment, HK cells were infected at a ratio of 27:1 (yeast to HK cell) for 8 hours in the presence or absence of 0.2 μM HPA3NT3 peptide, HPN3 peptide, or HP(2-20) peptide. After incubation, RNA was harvested and IL-8 transcriptional levels were assessed, with the data shown in FIG. 10A. Initially, *M. furfur* infection induced expression of IL-8 mRNA in HK cells by approximately 3.5-fold compared to uninfected HK cells. Conversely, treatment with the HPA3NT3 peptide significantly reduced the *M. furfur*—infection induced increase in IL-8 mRNA to levels less than that of uninfected HK cells. Similar inhibition was seen with the HP(2-20) peptide treatment. Moreover, use of the HPN3 peptide did not have an as significant impact on IL-8 mRNA.

Figure 10A:
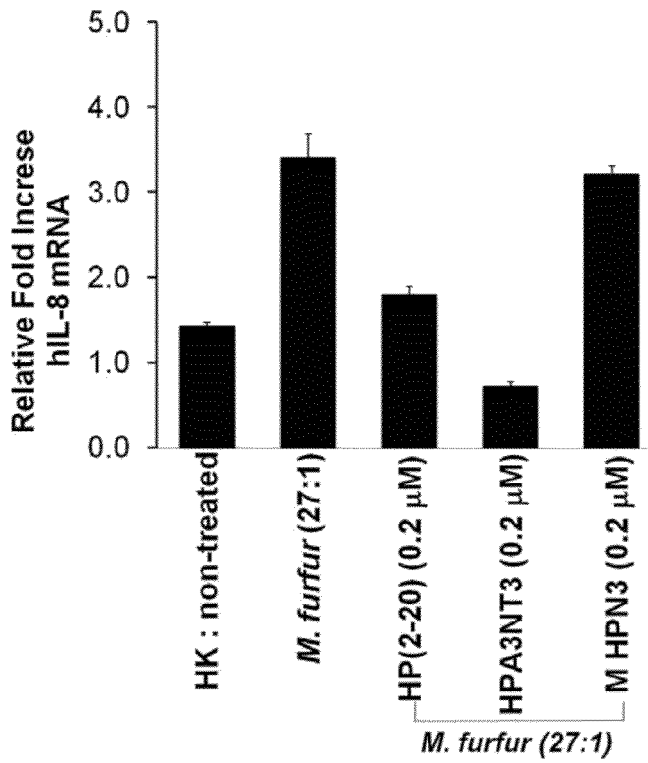
FIG. 10 graphically depicts HK cell IL-8 mRNA expression as measured by real-time RT-PCR (A) and the secretion of IL-8 protein as measured by ELISA (B) after infection with *M. furfur* and with or without HPA3NT3 peptide or HPN3 peptide. The data shown are representative of triplicate experiments. All values in these graphs are expressed as mean±standard deviation.
Figure 10B:
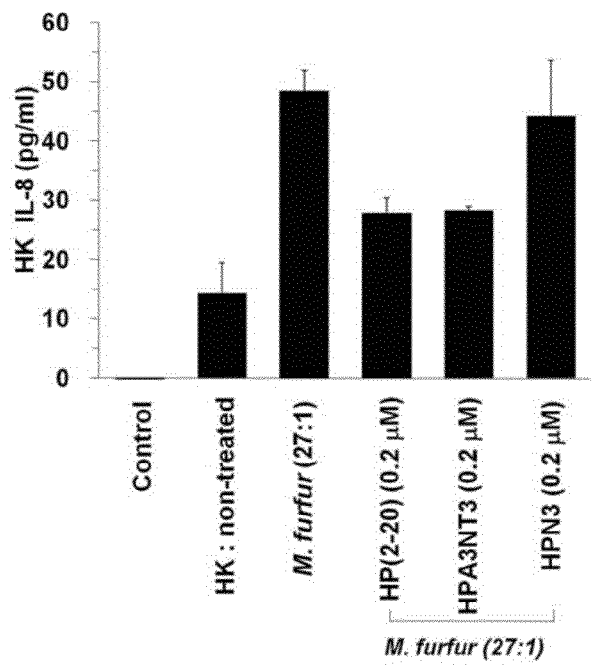

Similar experiments were repeated to assess the impact of *M. furfur* infection on IL-8 protein levels. In short, the same experiment discussed above with respect to *M. furfur* and IL-8 mRNA was repeated except that supernatants of the cell cultures were harvested at 24 hours after incubation and IL-8 protein levels were tested using an ELISA. In brief, the data noted above with respect to the transcriptional impact of HPA3NT3 peptide on *M. furfur*-infected HK cells is also correlated to protein levels. In particular, as shown in FIG. 10B, treatment of *M. furfur*-infected HK cells with HPA3NT3 peptide resulted in a reduction of infection-induced IL-8 protein in the cell supernatant. Accordingly, the data showed in FIGS. 10A and 10B illustrate that the HPA3NT3 peptide has an impact on inflammation that is not only induced by bacterial species (i.e., *P. acnes* and *P. aeruginosa*), but also other organisms, including fungi species (i.e., *M. furfur*).

Figure 11:
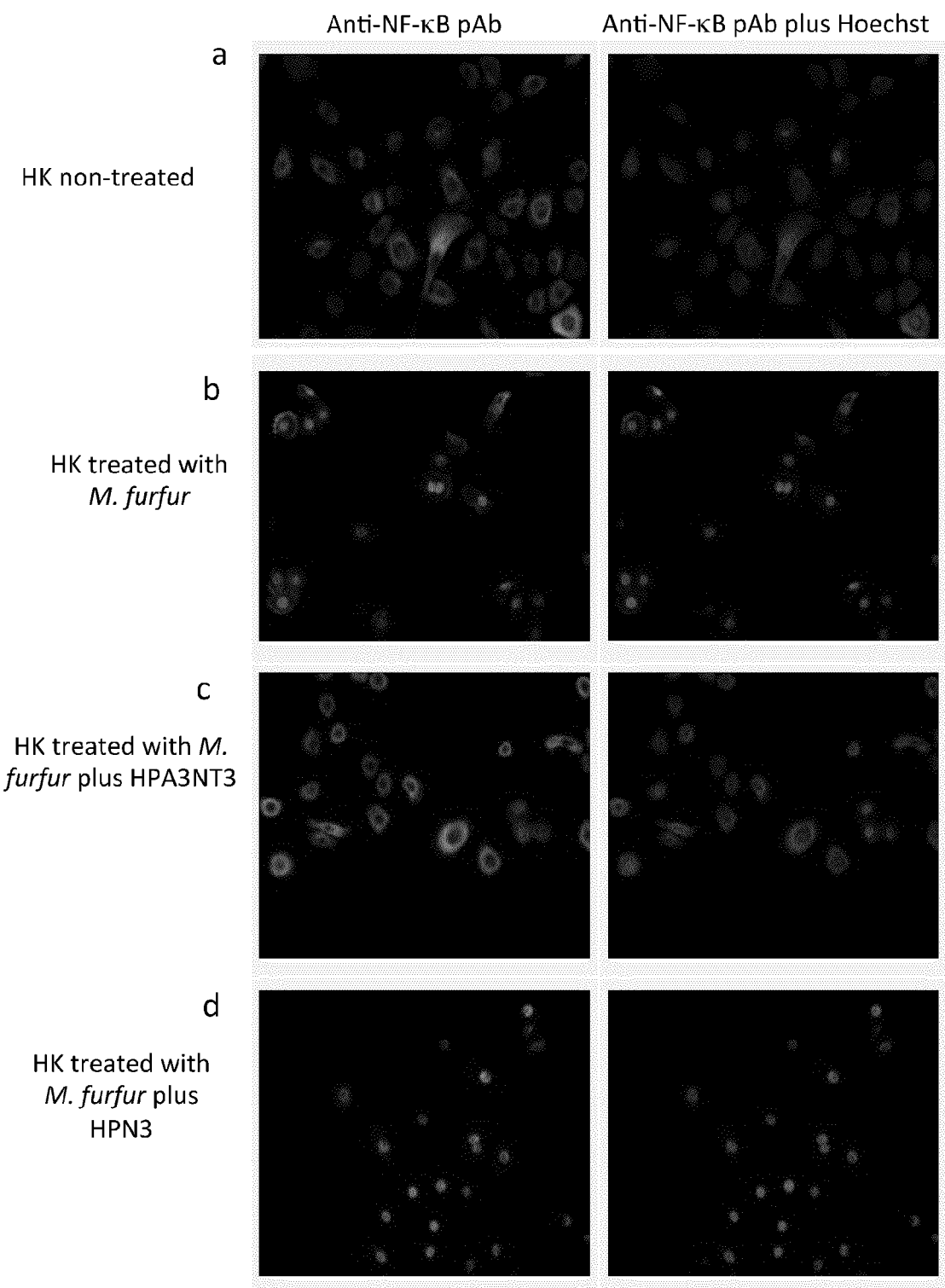
FIG. 11 depicts immunofluorescent staining of cellular NF-κB protein in HK cells that were uninfected (A), infected with *M. furfur* at a ratio of 27 yeast cells to one HK cell for 30 minutes (B), infected with *M. furfur* at a ratio of 27 yeast cells to one HK cell for 30 minutes and treated with 0.2 µM HPA3NT3 peptide (C), or infected with *M. furfur* at a ratio of 27 yeast cells to one HK cell for 30 minutes and treated with 0.2 µM HPN3 peptide (D).

HPA3NT3 Peptide Inhibits *M. furfur*-Induced HK Cell NF-κB Nuclear Translocation In order to assess the possible mechanism behind the impact of treatment with the HPA3NT3 peptide on *M. furfur*-infection induced IL-8 expression, an experiment was conducted to determine the impact of this treatment on NF-κB translocation. Accordingly, the localization of intracellular NF-κB was determined by immunofluorescence staining using an anti-NF-κB p65 polyclonal antibody, with the results of this experiment shown in FIG. 11. In this experiment, HK cells were incubated with or without the HPA3NT3 peptide and infected with *M. furfur* at a ratio of 27 yeast cells to one HK cell. Initially, in uninfected HK cells, the NF-κB p65 staining was primarily localized to the cytoplasm, as shown in FIG. 11A. However, nuclear translocation of NF-κB p65 was rapidly induced upon infection of the HK cells with *M. furfur*, as shown in FIG. 11B. Interestingly, co-incubation of HK cells with both *M. furfur* and the HPA3NT3 peptide resulted in an effective blocking of *M. furfur*-induced NF-κB p65 nuclear translocation, as shown in FIG. 11C. In contrast, when the HK cells were co-incubated with *M. furfur* and the HPN3 peptide (the negative control), nuclear translocation of NF-κB p65 was not blocked, as shown in FIG. 11D. Accordingly, this data further demonstrates that treatment with the HPA3NT3 peptide works to suppress the natural processes carried out by cells to produce an inflammatory response to a stimulus, in this case, a *M. furfur* infection.

Figure 12:
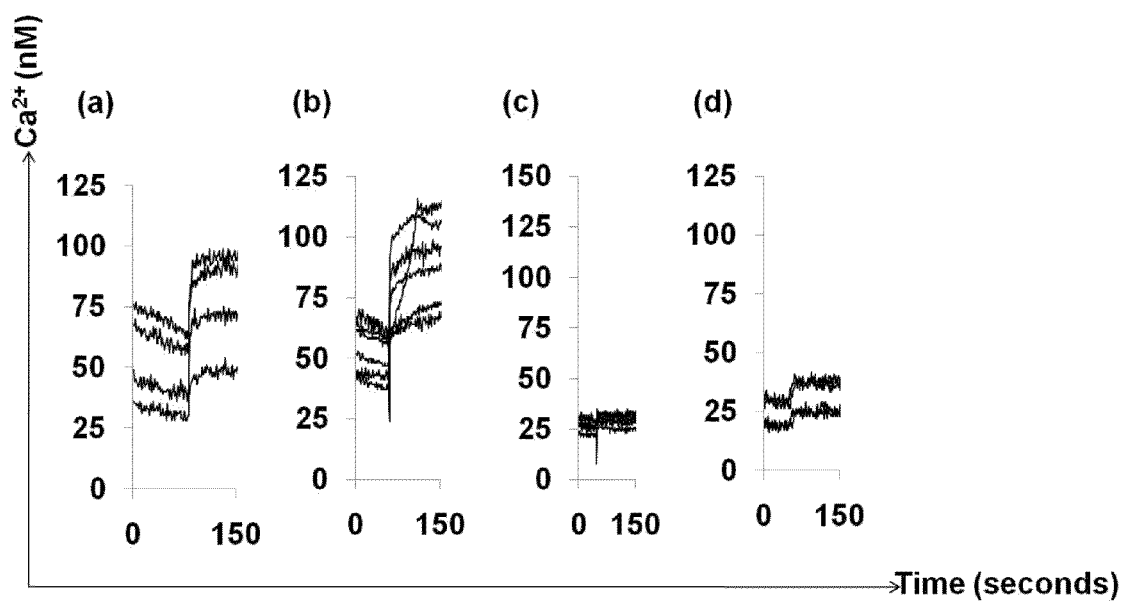
FIG. 12 depicts intracellular calcium fluctuations in HK cells that were infected with *M. furfur* at a ratio of 27 yeast cells to one HK cell for 2 hours in the absence (A) or presence of 0.2 µM HPA3NT3 peptide or HPN3 peptide (B) or uninfected HK cells in the presence of 0.2 µM HPA3NT3 peptide (C) of HPN3 peptide (D). Intracellular free calcium concentration (nM) was determined by measuring the ratio of fluorescence at excitation wavelengths of 340 and 380 nm. Each peak in the figure represents the rapid intracellular calcium response of individual cells.

HPA3NT3 Peptide Abrogates HK Cell Intracellular Calcium Fluctuation Induced by *M. furfur* Infection In this experiment, the role of the HPA3NT3 peptide was investigated in terms of its impact on intracellular calcium signaling during a *M. furfur* infection. In this experiment, HK cells were pre-incubated with or without HPA3NT3 peptide and then infected with *M. furfur* at a ratio of 27 yeast cells to one HK cell. Specifically, HK cells were grown on a glass coverslip in culture dishes to a confluence of between 50 and 70%. Then, 2 µM fluorescent calcium probe fura-2/AM was incorporated. Intracellular calcium fluctuation was measured as discussed above. As shown in FIG. 12A, in HK cells that were not pretreated with the HPA3NT3 peptide and infected with *M. furfur*, the infection resulted in a rapid intracellular calcium fluctuation. Conversely, as shown in FIG. 12B, pre-incubation with 0.2 µM HPA3NT3 peptide abrogated the *M. furfur*-infection induced intracellular calcium fluctuation. However, HK cells that were pre-incubated with the HPN3 peptide did not exhibit the abrogated intracellular calcium fluctuation noted in the HPA3NT3 peptide condition, as also shown in FIG. 12B. Stimulation with the HPA3NT3 peptide and the HPN3 peptide alone resulted in little intracellular calcium fluctuation, as shown in FIGS. 12C and 12D, respectively. This data shows that the HPANT3 peptide efficiently blocks a rapid fluctuation of intracellular calcium that is induced by a *M. furfur* infection, which further supports the conclusion that this peptide has a functional competence in non-immortalized cells.

Figure 13A:
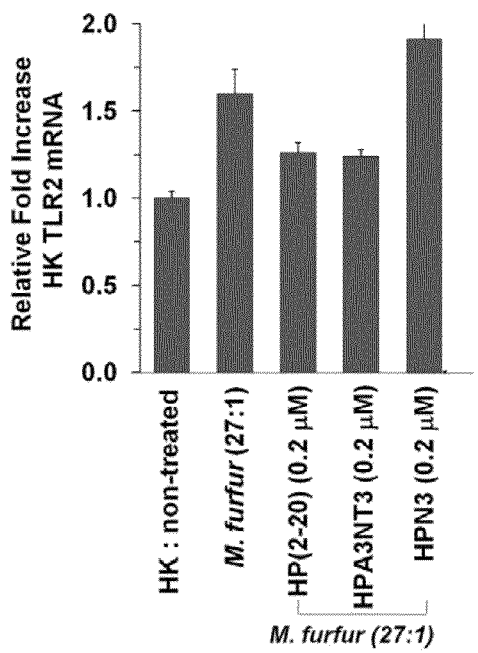
FIG. 13 depicts TLR2 mRNA expression as measured by real-time RT-PCR in HK cells after infection with *M. furfur* after 8 hours with or without 0.2 µM HPA3NT3 peptide, HP(2-20) peptide, or HPN3 peptide (A). Localization of TLR2 protein was determined by immunofluorescent staining in HK cells (B) that were uninfected (i), infected with *M. furfur* (ii), infected with *M. furfur* plus HPA3NT3 peptide (iii), and infected with *M. furfur* plus HPN3 peptide (iv).
Figure 13B:
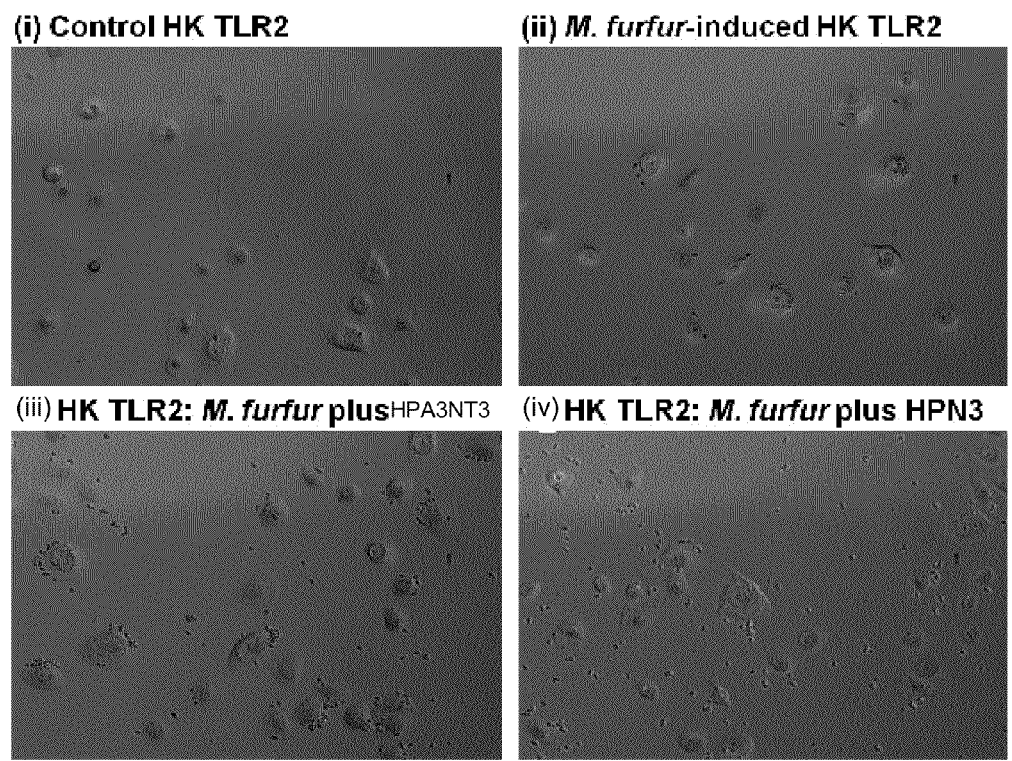

HPA3NT3 Peptide Significantly Inhibits the Expression of HK Cell TLR2 Induced by *M. furfur* Infection Next, an experiment was conducted to examine the functional role of the HPA3NT3 peptide in augmenting the expression of TLR2 in HK cells that are infected by *M. furfur*. In short, HK cells were infected with *M. furfur* (at a ratio of 27:1) for 8 hours and treated with 0.2 µM HPA3NT3 peptide, HPN3 peptide, HP(2-20) peptide or nothing, and mRNA was analyzed after the incubation period. As illustrated by the graph in FIG. 13A, TLR2 mRNA was increased by about 1.5-fold in HK cells 8 hours after *M. furfur* infection, relative to uninfected HK cells. In contrast, when HK cells were also treated with the HPA3NT3 peptide, the increase in TLR2 mRNA that resulted from the *M. furfur* infection was down-regulated. However, this down-regulation was not seen in cells that were treated with the HPN3 peptide. Similarly, as shown in FIGS. 13B(i)-13B(iv), treatment with the HPA3NT3 peptide effectively inhibited *M. furfur*-induced cellular expression of TLR2 protein compared to the negative control peptide, HPN3. This data again supports the conclusion that HPA3NT2 peptide reduces and/or treats inflammation that is caused by *M. furfur* infection.

It should be understood from the foregoing that, while particular embodiments have been illustrated and described, various modifications may be made thereto without departing from the spirit and scope of the invention as will be apparent to those skilled in the art. Such changes and modifications are within the scope and teachings of this invention as defined in the claims appended hereto.

What is claimed is:

1. A method of treating an infection and infection-induced inflammation in non-immortalized cells, the method comprising topically administering a therapeutically effective amount of an HPA3NT3 peptide.

2. The method of claim 1, wherein the non-immortalized cells are primary cells.

3. The method of claim 1, wherein the non-immortalized cells are at least one of keratinocytes, dermal microvascular endothelial cells, corneal epithelial cells, and dermal fibroblasts.

4. The method of claim 1, wherein the infection is a bacterial infection.

5. The method of claim 4, wherein the bacteria causing the bacterial infection is at least one of *Propionibacterium acnes*, *Staphylococcus aureus*, or *Pseudomonas aeruginosa*.

6. The method of claim 5, wherein the *Pseudomonas aeruginosa* bacteria are resistant to more than one antibiotic.

7. The method of claim 6, wherein the therapeutically effective amount of HPA3NT3 peptide functions as a bactericidal agent.

8. A method of reducing expression of at least one pro-inflammatory cytokine by a non-immortalized cell, the method comprising topically administering a therapeutically effective amount of an HPA3NT3 peptide to the cell.

* * * * *

SEQUENCE LISTING

```
<160> NUMBER OF SEQ ID NOS: 7

<210> SEQ ID NO 1
<211> LENGTH: 15
<212> TYPE: PRT
<213> ORGANISM: Helicobacter pylori

<400> SEQUENCE: 1

Phe Lys Arg Leu Lys Lys Leu Phe Lys Lys Ile Trp Asn Trp Lys
1               5                   10                  15

<210> SEQ ID NO 2
<211> LENGTH: 21
<212> TYPE: DNA
<213> ORGANISM: Homo sapiens

<400> SEQUENCE: 2
gcagttttgc caaggagtgc t                                        21

<210> SEQ ID NO 3
<211> LENGTH: 21
<212> TYPE: DNA
<213> ORGANISM: Homo sapiens

<400> SEQUENCE: 3
tttctgtgtt ggcgcagtgt g                                        21

<210> SEQ ID NO 4
<211> LENGTH: 20
<212> TYPE: DNA
<213> ORGANISM: Homo sapiens

<400> SEQUENCE: 4
tgtcttgtga ccgcaatggt                                          20
```

```
<210> SEQ ID NO 5
<211> LENGTH: 21
<212> TYPE: DNA
<213> ORGANISM: Homo sapiens

<400> SEQUENCE: 5
tgttggacag gtcaaggctt t                                              21

<210> SEQ ID NO 6
<211> LENGTH: 17
<212> TYPE: DNA
<213> ORGANISM: Homo sapiens

<400> SEQUENCE: 6
cggctacatc caaggaa                                                   17

<210> SEQ ID NO 7
<211> LENGTH: 18
<212> TYPE: DNA
<213> ORGANISM: Homo sapiens

<400> SEQUENCE: 7
gctggaatta ccgcggct                                                  18
```